(12) United States Patent
Bell et al.

(10) Patent No.: US 10,206,388 B2
(45) Date of Patent: Feb. 19, 2019

(54) FORMULATION COMPONENT

(75) Inventors: Gordon Alastair Bell, Bracknell (GB); Julia Lynne Ramsay, Bracknell (GB); Raul Minguez Molina, Bracknell (ES); David Stock, Bracknell (GB); Gary Charles Walter, Bracknell (GB)

(73) Assignee: SYNGENTA LIMITED, Guildford, Surrey (GB)

( * ) Notice: Subject to any disclaimer, the term of this patent is extended or adjusted under 35 U.S.C. 154(b) by 218 days.

(21) Appl. No.: 14/113,678

(22) PCT Filed: Apr. 13, 2012

(86) PCT No.: PCT/GB2012/000341
§ 371 (c)(1),
(2), (4) Date: Jan. 13, 2014

(87) PCT Pub. No.: WO2012/146889
PCT Pub. Date: Nov. 1, 2012

(65) Prior Publication Data
US 2014/0113823 A1  Apr. 24, 2014

(30) Foreign Application Priority Data
Apr. 26, 2011 (GB) .................... 1107039.8

(51) Int. Cl.
| A01N 25/00 | (2006.01) |
| A01N 43/56 | (2006.01) |
| A01N 43/653 | (2006.01) |
| A01N 37/10 | (2006.01) |
| A01N 37/14 | (2006.01) |
| A01N 41/06 | (2006.01) |
| A01N 41/10 | (2006.01) |
| A01N 43/54 | (2006.01) |
| A01N 43/90 | (2006.01) |

(52) U.S. Cl.
CPC ............ *A01N 25/00* (2013.01); *A01N 37/10* (2013.01); *A01N 37/14* (2013.01); *A01N 41/06* (2013.01); *A01N 41/10* (2013.01); *A01N 43/54* (2013.01); *A01N 43/56* (2013.01); *A01N 43/653* (2013.01); *A01N 43/90* (2013.01)

(58) Field of Classification Search
CPC ...... A01N 47/36; A01N 41/06; A01N 43/653; A01N 43/90; A01N 2300/00; A01N 45/02; A01N 37/10; A01N 37/14; A01N 41/10; A01N 25/00; A01N 43/54; A01N 43/56; C03C 1/006
USPC .......... 504/215, 219, 333, 348; 514/30, 383, 514/406
See application file for complete search history.

(56) References Cited

U.S. PATENT DOCUMENTS

| 4,245,030 A | 1/1981 | Faust et al. |
| 4,791,097 A | 12/1988 | Walele |
| 5,271,930 A | 12/1993 | Walele |
| 5,626,859 A * | 5/1997 | Fitch et al. .................... 424/409 |
| 2002/0098221 A1* | 7/2002 | Taranta .................. A01N 25/04 424/405 |
| 2009/0270259 A1* | 10/2009 | Auweter ................ A01N 25/04 504/359 |

FOREIGN PATENT DOCUMENTS

| CN | 10033801 | * | 9/2007 | |
| EP | 0974575 | | 1/2000 | |
| EP | 140322 | | 3/2004 | |
| GB | 2181429 | | 4/1997 | |
| JP | 50059516 | | 5/1975 | |
| JP | 3050246 | | 3/1991 | |
| JP | 3050266 | | 3/1991 | |
| JP | 3059045 | | 3/1991 | |
| JP | 5339413 | | 12/1993 | |
| JP | 8127964 | | 5/1996 | |
| JP | 200459517 | | 2/2004 | |
| JP | 200467756 | | 3/2004 | |
| WO | WO9517817 | | 7/1995 | |
| WO | WO0209519 | | 2/2002 | |
| WO | WO 0209519 A1 | * | 2/2002 | |
| WO | 2010115721 | | 10/2010 | |
| WO | WO 2011015220 A1 | * | 2/2011 | ............. A01N 43/90 |

OTHER PUBLICATIONS

Finsolv TPP, Jan. 1, 2008, XP007907237, Retrieved from the Internet: URL: http://www.innospecinc.com/assets/_files_documents/may_08/cm_1210344975_Finsolv.TPP.pdf.

Steinbeck, K. et al., "Baseninduzierte ringoffnung von 1, 3-dioxolanen: ein neuer weg zu dienolethern", Tetrahedron Letters, 21(16), Jan. 1, 1980, pp. 1515-1518, XP55032338.

* cited by examiner

*Primary Examiner* — Johann R Richter
*Assistant Examiner* — Courtney A Brown
(74) *Attorney, Agent, or Firm* — Dinsmore & Shohl LLP; Toni-Junell Herbert

(57) ABSTRACT

This invention relates to the use of aromatic esters as adjuvants in compositions, particularly for agrochemical use, as well to compositions comprising such an aromatic ester, in combination with at least one agrochemical and at least one surfactant. The invention further extends to methods of making and using such compositions. In particular the present invention relates to such compositions when formulated as, or comprised by, an emulsion concentrate (EC), an emulsion in water (EW), a suspension of particles in water (SC), a microcapsule formulation (CS), a suspension of particles with an emulsion (SE), a dispersion concentrate (DC) or an oil suspension (OD).

21 Claims, No Drawings

FORMULATION COMPONENT

RELATED APPLICATION INFORMATION

This application claims priority under 35 U.S.C. § 371 from PCT Application No. PCT/GB2012/000341, filed 13 Apr. 2012, which claims the benefit of European Patent Application 1107039.8, filed 26 Apr. 2011, the disclosures of which are incorporated by reference herein.

This invention relates to the use of aromatic esters as adjuvants in compositions, particularly for agrochemical use, as well to compositions comprising such an aromatic ester, in combination with at least one agrochemical and at least one surfactant. The invention further extends to methods of making and using such compositions. In particular the present invention relates to such compositions when formulated as, or comprised by, an emulsion concentrate (EC), an emulsion in water (EW), a suspension of particles in water (SC), a microcapsule formulation (CS), a suspension of particles with an emulsion (SE), a dispersion concentrate (DC) or an oil suspension (OD).

The efficacy of the active ingredients (AIs) in an agrochemical composition can often be improved by the addition of further ingredients. The observed efficacy of the combination of ingredients can sometimes be significantly higher than that which would be expected from the individual ingredients used (synergism). An adjuvant is a substance which can increase the biological activity of and AI but is itself not significantly biologically active. The adjuvant is often a surfactant, and can be included in the formulation or added separately, e.g. by being built into emulsion concentrate formulations, or as tank mix additives.

In addition to the effect on biological activity, the physical properties of an adjuvant are of key importance and must be selected with a view to compatibility with the formulation concerned. For instance, it is generally simpler to incorporate a solid adjuvant into a solid formulation such as a water-soluble or water-dispersible granule. In general adjuvants rely on surfactant properties for biological activity enhancement and one typical class of adjuvants involves an alkyl or aryl group to provide a lipophilic moiety and a (poly)ethoxy chain to provide a hydrophilic moiety. Much has been published on the selection of adjuvants for various purposes, such as Hess, F. D. and Foy, C. L., Weed technology 2000, 14, 807-813.

The present invention is based on the discovery that aromatic esters with relatively long hydrocarbon chains are surprisingly effective adjuvants, significantly enhancing the biological activity of active ingredients. Aromatic esters of varied hydrocarbon chain lengths have until now only been known as solvents (such as Benzoflex 181™ and Finsolv® TN), emollients and thickening agents for use in various industries. There is also a meager amount of information presently available on preferentially shorter chain aromatic esters having putative adjuvant properties in the context of agrochemical compositions.

According to the present invention, there is provided an agrochemical composition comprising:

i. an active ingredient ii. a surfactant iii. an aromatic ester of formula (I)

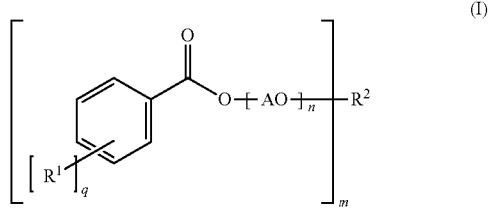

(I)

wherein
$R^1$ is OH, halogen, or di-$C_{1-4}$alkyl amino,
q is 0 or 1
n is an integer selected from 0 to 20 inclusive,
each A is independently $C_{1-10}$alkanediyl,
m is an integer selected from 1, 2 and 3;
wherein when m is 1, $R^2$ is selected from the group consisting of $C_7$-$C_{20}$alkyl, $C_7$-$C_{20}$ alkenyl, $C_7$-$C_{20}$ alkyldienyl and $C_7$-$C_{20}$ alkyltrienyl; and when m is 2 or 3, $R^2$ is selected from the group consisting of $C_r$-$C_{20}$ alkyl, $C_4$-$C_{22}$ alkenyl, $C_4$-$C_{22}$ alkyldienyl and $C_6$-$C_{22}$ alkyltrienyl; and
each group

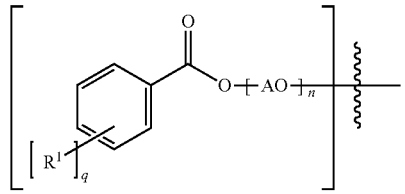

is independently attached to any carbon atom within $R^2$, and each $R^1$, q, A and n is independently as defined above provided that the compound of formula (I) is not dipropylene glycol dibenzoate.

In a second aspect the invention provides for the use of an aromatic ester of formula (I) as described herein as an adjuvant in an agrochemical composition.

In a third aspect the invention provides for the use of an agrochemical composition as described herein to control pests.

In a further aspect there is provided a method of controlling a pest, comprising applying a composition of the invention to said pest or to the locus of said pest.

In yet a further aspect there is provided a method of making an agrochemical composition as described herein, comprising combining an active ingredient, a surfactant and an aromatic ester of formula (I).

Alkyl groups and moieties are straight or branched chains, and unless explicitly stated to the contrary, are unsubstituted. Examples of suitable alkyl groups for use in the invention are hexyl, heptyl, octyl, nonyl, decyl, undecyl, dodecyl, tridecyl, tetradecyl, pentadecyl, hexadecyl, heptadecyl, octadecyl, nonadecyl and eicosyl groups.

Alkenyl groups and moieties are straight or branched chains having a single carbon-carbon double bond, and unless explicitly stated to the contrary, are unsubstituted. Examples of suitable alkenyl groups for use in the invention are hept-1-enyl, hept-2-enyl, hept-3-enyl, oct-1-enyl, non-1-enyl, dec-1-enyl, undec-1-enyl, and groups derived from monoenoic fatty acids including cis-4-decenyl, cis-9-decenyl, cis-5-laurolyl, cis-4-dodecenyl, cis-9-tetradecenyl, cis-5-tetradecenyl, cis-4-tetradecenyl, cis-9-hexadecenyl, cis-6-hexadecenyl, cis-6-octadecenyl, cis-9-octadecenyl, trans-9- octadecenyl, cis-11-octadecenyl, cis-9-eicosenyl, cis-11-eicosenyl, cis-11-docosenyl, cis-13-docosenyl and cis-15-tetracosenyl.

Alkyldienyl groups and moieties are straight or branched chains having two carbon-carbon double bond, and unless explicitly stated to the contrary, are unsubstituted. Examples of suitable alkyldienyl groups for use in the invention are hept-1,3-dienyl, linoleyl, and linoelaidyl.

Alkyltrienyl groups and moieties are straight or branched chains having three carbon-carbon double bond, and unless explicitly stated to the contrary, are unsubstituted. Examples of suitable alkyldienyl groups for use in the invention hex-1,3,5-trienyl, hepta-1,3,5-trienyl, and linolenyl.

The term alkanediyl defines bivalent straight or branch chained hydrocarbon radicals such as, for example, methylene, 1,2-ethanediyl, 1,1-ethanediyl, 1,3-propanediyl, 1,1-propanediyl, 1,2-propanediyl, 1,4-butanediyl, 1,5-pentanediyl and the like.

The term halogen includes F, Cl, Br, and I, with fluorine and chlorine being particularly preferred halogens.

In particularly preferred embodiments of the invention, the preferred values for m, n, and q, as well as the preferred groups for $R^1$ and $R^2$, in any combination thereof (unless specifically stated otherwise) are as set out below.

As stated above, $R^1$ may be a hydroxyl group, a halogen, or a di-$C_{1-4}$ alkyl amino group wherein each alkyl is independently $C_1$-$C_4$ alkyl. Preferably $R^1$ is a di-$C_1$-$C_4$ alkyl amino group, and in particular a di $C_1$-$C_4$ alkyl amino group wherein each alkyl group is independently methyl, ethyl, propyl or butyl, more preferably methyl or ethyl, and most preferably each alky group is methyl. In an alternative preferred embodiment, $R^1$ is hydroxy, preferably 2-hydroxy.

Where q is 1, $R^1$ is preferably at the 4 position of the phenyl ring. In certain embodiments it is preferred that q is 0.

As stated above, each A is independently a $C_1$-$C_{10}$ alkanediyl group. Preferably each A is independently a $C_1$-$C_4$ alkanediyl group, more preferably each A is independently ethanediyl, propanediyl, butanediyl, or butanediyl, more preferably still each A is independently 1,2-ethanediyl, 1,2-propanediyl, 1,2-butanediyl, or 1,4-butanediyl. 1,2-ethanediyl is most preferred.

According to the invention, n is an integer selected from 0 to 20 inclusive. Preferably n is an integer selected from 0-10 inclusive, more preferably 0-5 inclusive, even more preferably n is 0, 1, 2, or 3, and most preferably n is 0, or 1.

The value of m is 1, 2 or 3.

In certain embodiments, where m is 1, $R^2$ is H, or $C_7$-$C_{20}$ alkyl. More preferably in such embodiments $R^2$ is $C_8$-$C_{18}$ alkyl, more preferably $C_8$-$C_{15}$ alkyl, and more preferably still, $C_{12}$-$C_{15}$ alkyl. In specific embodiments when m is 1, $R^2$ is 2-ethyl hexyl, $C_{12}$ alkyl, $C_{13}$ alkyl, $C_{14}$ alkyl, $C_{15}$ alkyl, $C_{16}$ alkyl, $C_{17}$ alkyl, oleyl or isoocatadecyl.

In other embodiments where m is 2 or 3, the skilled man will appreciate that each group

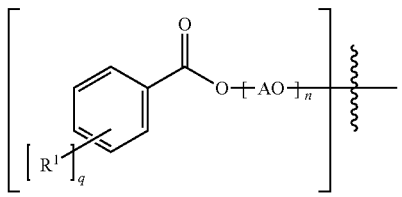

may be the same or different (i.e. each $R^1$, q, A and n is independently as defined hereinbefore), furthermore, each group

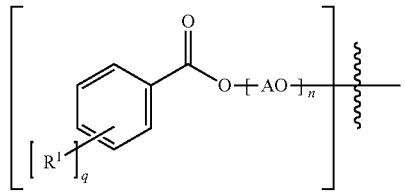

is independently attached to any carbon atom in $R^2$, and $R^2$ is $C_1$-$C_{20}$ alkyl. In certain of these embodiments, $R^2$ is at least a $C_2$ alkyl group, and each group

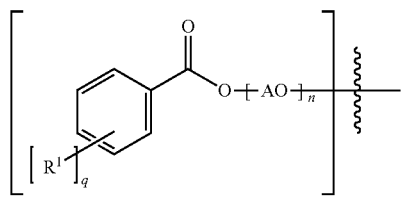

is attached to a different carbon atom in $R^2$.

In further embodiments, when m is 2 or 3, $R^2$ is $C_7$-$C_{18}$ alkyl, more preferably, $C_8$-$C_{17}$ alkyl, more preferably $C_8$ alkyl, $C_{12}$-$C_{15}$ alkyl, $C_{16}$ alkyl, or $C_{17}$ alkyl. In certain embodiments wherein m is 2, $R^2$ is a $C_8$ branched chain alkyl group.

In one embodiment, there is provided an agrochemical composition comprising. (i) an active ingredient, (ii) a surfactant, and (iii) an aromatic ester of formula (I)

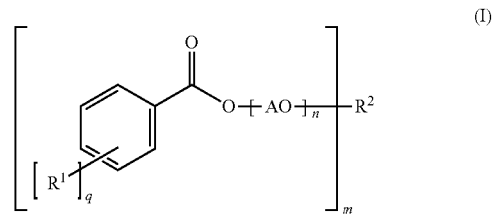

wherein $R^1$ is di-$C_1$-$C_4$alkyl amino, hydroxyl, or halogen, q is an integer selected from 0 or 1, n is an integer selected from 0 to 20 inclusive, each A is independently $C_{1-10}$ alkyl, m is an integer selected from 1, 2 and 3; and wherein when m is 2 or 3, $R^2$ is $C_1$-$C_{20}$ alkyl; each group

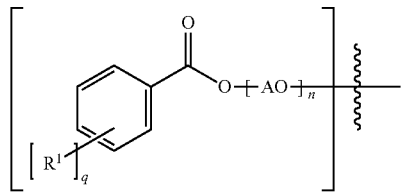

is independently attached to any carbon atom within $R^2$, and each $R^2$, q, A and n is independently as defined above provided that the compound of formula (I) is not dipropylene glycol dibenzoate, and when m is an integer selected from 1, $R^2$ is H or $C_7$-$C_{20}$ alkyl.

Certain compounds of formula (I) are available commercially and include for example, those described in Table 1 below which are given a trade name. Other compounds are novel, and form a separate aspect of the invention.

TABLE 1

Compounds of formula (I) for use in the invention

| Compound | Trade name | Suppliers | CAS no. |
|---|---|---|---|
| $C_{12}$-$C_{15}$ alkyl benzoate | Finsolv ® Tn | Innospec | 68411-27-8 |
| Isostearyl benzoate | Finsolv ® SB | Innospec | 34364-24-4 |
| 2-ethylhexyl benzoate | Benzoflex 181 | Eastman Chemical Company | 5444-75-7 |
| 2,2,4-trimethyl-1,3-pentanediol dibenzoate | Benzoflex 354 | Eastman Chemical Company, Sigma Aldrich | 68052-23-3 |
| 2-ethylhexyl-4-(dimethylamino)benzoate | Escalol ® 507 | International Specialty Products | 21245-02-3 |
| $C_{12}$-$C_{15}$ ethoxy benzoate - degree of ethoxylation = 3 | Dermol ®25-3B | Alzo International Inc | |
| Tridecyl salicylate | | | 19666-16-1 |
| Oleth-2 benzoate | | | |
| Oleth-10 benzoate | | | |
| Oleth-20 benzoate | | | |
| Oleth-12 benzoate | | | |
| Isosteareth-12 benzoate | | | |
| Isosteareth-10 benzoate | | | |
| Trideceth-5 benzoate | | | |

Alternatively, aromatic esters of formula (I) may be prepared using well know reactions. See reaction schemes 1 and 2 below.

Reaction scheme 1

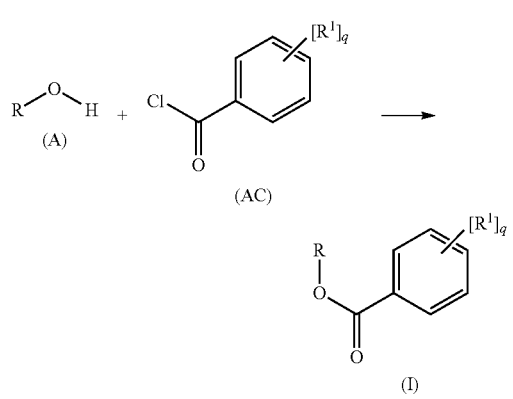

An alcohol of formula (A) is reacted with an acid chloride of formula (AC) in order to form a benzoic acid ester of formula (I), in which $R^1$ and q are as defined hereinbefore, and R represents the group -[AO]$_n$—$R^2$ wherein A, n and $R^2$ are as defined hereinbefore. This general reaction scheme was followed in Example 9.

Reaction scheme 2

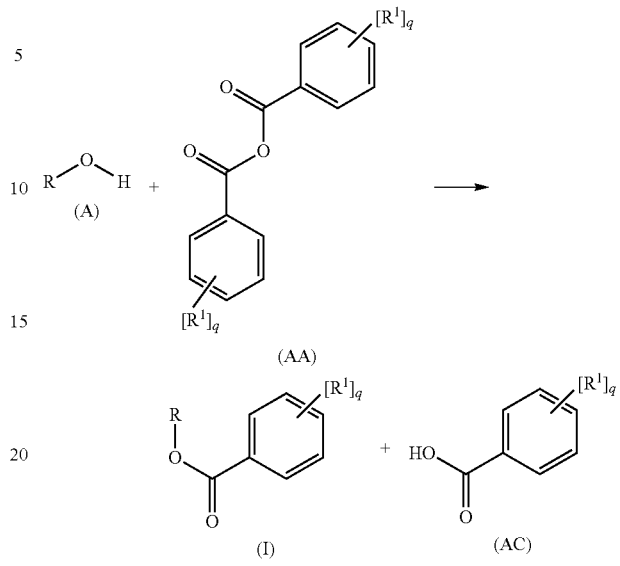

An alcohol of formula (A) is reacted with an acid anhydride of formula (AA) to form a benzoic acid ester of formula (I) plus an acid of formula (AC). $R^1$ and q are as defined hereinbefore, and R represents the group -[AO]$_n$—$R^2$ wherein A, n and $R^2$ are as defined hereinbefore.

Alcohols of formula (A), acid chlorides of formula (AC) and acid anhydrides of formula (AA) are readily available or may be synthesised using standard methodology well known in the art.

As stated previously, the present invention is based on the unexpected finding that compounds of formula (I) are particularly good adjuvants in agrochemical formulations. Accordingly, in one aspect, the invention provides the use of an aromatic ester of formula (I) as described herein as a synergist in an agrochemical composition Accordingly, such adjuvants may be combined with an active ingredient, which is an agrochemical, in order to form an agrochemical composition. The present invention extends to a method of making such an agrochemical composition, wherein said method comprises combining a compound of formula (I) with an agrochemically active ingredient, and optionally a surfactant. The noun "agrochemical" and term "agrochemically active ingredient" are used herein interchangeably, and they include herbicides, insecticides, nematicides, molluscicides, funcgicides, plant growth regulators, and safeners, preferably herbicides, insecticides, and funcgicides.

Suitable herbicides include bicyclopyrone, mesotrione, fomesafen, tralkoxydim, napropamide, amitraz, propanil, pyrimethanil, dicloran, tecnazene, toclofos methyl, flamprop M, 2,4-D, MCPA, mecoprop, clodinafop-propargyl, cyhalofop-butyl, diclofop methyl, haloxyfop, quizalofop-P, indol-3-ylacetic acid, 1-naphthylacetic acid, isoxaben, tebutam, chlorthal dimethyl, benomyl, benfuresate, dicamba, dichlobenil, benazolin, triazoxide, fluazuron, teflubenzuron, phenmedipham, acetochlor, alachlor, metolachlor, pretilachlor, thenylchlor, alloxydim, butroxydim, clethodim, cyclodim, sethoxydim, tepraloxydim, pendimethalin, dinoterb, bifenox, oxyfluorfen, acifluorfen, fluoroglycofenethyl, bromoxynil, ioxynil, imazamethabenz-methyl, imazapyr, imazaquin, imazethapyr, imazapic, imazamox, flumioxazin, flumiclorac-pentyl, picloram, amodosulfuron, chlorsulfuron, nicosulfuron, rimsulfuron, triasulfuron, triallate, pebulate, prosulfocarb, molinate, atrazine, simazine, cyanazine, ametryn, prometryn, terbuthylazine, terbutryn, sulcotrione, isoproturon, linuron, fenuron, chlorotoluron and metoxuron.

Suitable fungicides include isopyrazam, mandipropamid, azoxystrobin, trifloxystrobin, kresoxim methyl, famoxadone, metominostrobin and picoxystrobin, cyprodanil, carbendazim, thiabendazole, dimethomorph, vinclozolin, iprodione, dithiocarbamate, imazalil, prochloraz, fluquinconazole, epoxiconazole, flutriafol, azaconazole, bitertanol, bromuconazole, cyproconazole, difenoconazole, hexaconazole, paclobutrazole, propiconazole, tebuconazole, triadimefon, trtiticonazole, fenpropimorph, tridemorph, fenpropidin, mancozeb, metiram, chlorothalonil, thiram, ziram, captafol, captan, folpet, fluazinam, flutolanil, carboxin, metalaxyl, bupirimate, ethirimol, dimoxystrobin, fluoxastrobin, orysastrobin, metominostrobin and prothioconazole.

Suitable insecticides include thiamethoxam, imidacloprid, acetamiprid, clothianidin, dinotefuran, nitenpyram, fipronil, abamectin, emamectin, bendiocarb, carbaryl, fenoxycarb, isoprocarb, pirimicarb, propoxur, xylylcarb, asulam, chlorpropham, endosulfan, heptachlor, tebufenozide, bensultap, diethofencarb, pirimiphos methyl, aldicarb, methomyl, cyprmethrin, bioallethrin, deltamethrin, lambda cyhalothrin, cyhalothrin, cyfluthrin, fenvalerate, imiprothrin, permethrin and halfenprox.

Suitable plant growth regulators include paclobutrazole and 1-methylcyclopropene.

Suitable safeners include benoxacor, cloquintocet-mexyl, cyometrinil, dichlormid, fenchlorazole-ethyl, fenclorim, flurazole, fluxofenim, mefenpyr-diethyl, MG-191, naphthalic anhydride, and oxabetrinil.

Preferred agrochemical active ingredients are isopyrazam, epoxyconazole, fomesafen, mesotrione, pinoxaden, abamectin and nicosulfuron.

Of course, the various editions of The Pesticide Manual [especially the 14$^{th}$ and 15$^{th}$ editions] also disclose details of agrochemicals, any one of which may suitably be used with the present invention.

The skilled man will appreciate that compositions of the invention may comprise one or more of the agrochemicals as described above.

Compositions of the invention will typically comprise the agrochemical in an amount that is recommended in the art. Generally the agrochemical will be present at a concentration of about 0.001% to 90% w/w. The skilled man will appreciate that compositions of the invention may be in the form of a ready-to-use formulation or in concentrate form suitable for further dilution by the end user, and the concentration of agrochemical and compound of formula (I) will be adjusted accordingly. In concentrated form, compositions of the invention typically comprise agrochemical at 5 to 75% w/w, more preferably 10 to 50% w/w agrochemical. Ready-to-use compositions of the invention will typically comprise from 0.0001% to 1% w/w, more preferably from 0.001% to 0.5% w/w, and more preferably still from 0.001% to 0.1% w/w agrochemical.

Typically a compound of formula (I) will comprise from about 0.0005% to about 90% w/w of the total composition. When in concentrated form, compositions of the invention typically comprise a compound of formula (I) from 1% to 80% w/w, preferably from 5% to 60% w/w and more preferably from 10% w/w to 40% w/w. Ready to use compositions of the invention typically comprise a compound of formula (I) from about 0.05% to about 1% w/w of the total composition, more preferably still from about 0.1% to about 0.5% w/w of the total composition. In specific embodiments the aromatic ester will be included at concentrations of 0.1%, 0.2%, 0.25%, 0.3%, 0.4% or 0.5% w/w of the total composition. Compounds of formula (I) may be manufactured and/or formulated separately, and in order to be used as an adjuvant these may be added to a separate agrochemical formulation at a subsequent stage, typically immediately prior to use.

Compositions of the invention may be formulated in any suitable manner known to the man skilled in the art. As mentioned above, in one form a composition of the invention is a formulation concentrate which may be diluted or dispersed (typically in water) by an end-user (typically a farmer) in a spray tank prior to application.

Additional formulation components may be incorporated alongside compounds of formula (I) or compositions of the invention in such formulations. Such additional components include, for example, adjuvants, surfactants, emulsifiers, and solvents, and are well known to the man skilled in the art: standard formulation publications disclose such formulation components suitable for use with the present invention (for example, Chemistry and Technology of Agrochemical Formulations, Ed. Alan Knowles, published by Kluwer Academic Publishers, The Netherlands in 1998; and Adjuvants and Additives: 2006 Edition by Alan Knowles, Agrow Report DS256, published by Informa UK Ltd, December 2006). Further standard formulation components suitable for use with the present invention are disclosed in WO2009/130281A1 (see from page 46, line 5 to page 51, line 40).

Thus, compositions of the present invention may also comprise one or more surfactants or dispersing agents to assist the emulsification of the agrochemical on dispersion or dilution in an aqueous medium (dispersant system). The emulsification system is present primarily to assist in maintaining the emulsified agrochemical in water. Many individual emulsifiers, surfactants and mixtures thereof suitable for forming an emulsion system for an agrochemical are known to those skilled in the art and a very wide range of choices is available. Typical surfactants that may be used to form an emulsifier system include those containing ethylene oxide, propylene oxide or ethylene oxide and propylene oxide; aryl or alkylaryl sulphonates and combinations of these with either ethylene oxide or propylene oxide or both; carboxylates and combinations of these with either ethylene oxide or propylene oxide or both. Polymers and copolymers are also commonly used.

Compositions of the present invention may also include solvents, which may have a range of water solubilitites. Oils with very low water solubilities may be added to the solvent of the present invention for assorted reasons such as the provision of scent, safening, cost reduction, improvement of the emulsification properties and alteration of the solubilising power. Solvents with higher water solubility may also be added for various reasons, for instance to alter the ease with which the formulation emulsifies in water, to improve the solubility of the pesticide or of the other optional additives in the formulation, to change the viscosity of the formulation or to add a commercial benefit.

Other optional ingredients which may be added to the formulation include for example, colourants, scents, and other materials which benefit a typical agrochemical formulation.

Compositions of the invention may formulated for example, as emulsion or dispersion concentrates, emulsions in water or oil, as a suspension of particles in an emulsion or oil, as microencapsulated formulations, aerosol sprays or fogging formulations; and these may be further formulated into granular materials or powders, for example for dry application or as water-dispersible formulations. Preferably compositions of the invention will be formulated as, or comprised by an emulsion concentrate (EC), an emulsion in water (EW), a microcapsule formulation (CS), a suspension of particles with an emulsion of oil (suspoemulsion; SE), a dispersion concentrate (DC) or an oil suspension (OD).

Compositions of the invention may be used to control pests. The term "pest" as used herein includes insects, fungi, molluscs, nematodes, and unwanted plants. Thus, in order to control a pest a composition of the invention may be applied directly to the pest, or to the locus of a pest.

Compositions of the invention also have utility in the seed treatment arena, and thus may be applied as appropriate to seeds.

The skilled man will appreciate that the preferences described above with respect to various aspects and embodiments of the invention may be combined in whatever way is deemed appropriate.

Various aspects and embodiments of the present invention will now be illustrated in more detail by way of example. It will be appreciated that modification of detail may be made without departing from the scope of the invention.

EXAMPLES

Example 1 Use of Benzoic Acid Ester Adjuvants in Agrochemical Compositions Comprising Isopyrazam The efficacy of the following benzoic acid esters Finsolv® TN ($C_{12}$-$C_{15}$ alkyl benzoate), Benzoflex 181 (2-ethylhexylbenzoate), methyl benzoate, and butyl benzoate, as adjuvants in compositions comprising isopyrazam was tested and compared to the standard formulations (both EC and SC) of the fungicide, which lack this type of adjuvant.

Wheat plants were inoculated with the fungus Septoria tritici. Four days after inoculation the plants were sprayed with a diluted emulsion concentrate or suspension concentrate formulation of the fungicide isopyrazam at rates of 3, 10, 30 and 100 mg of the fungicide per liter of spray solution, using a laboratory track sprayer which delivered the spray at a rate of 200 liters per hectare. Spray tests were also carried out with diluted suspension concentrate additionally comprising each of the benzoate adjuvants described above. These adjuvants were added to the spray solution at a rate of 0.2% w/w, based on the quantity of spray liquor. The leaves of the plants were assessed visually 14 days after the spray application and the damage was expressed as the percentage of the leaf area infected. Each spray test was replicated three times across the four application rates and the modelled means of these results are shown in Table 2 below.

As can be seen from Table 2 the inclusion of a benzoate as an adjuvant for isopyrazam resulted in a significant reduction in the percentage of infection by S. tritici in comparison to that achieved by the standard isopyrazam SC. Furthermore, the $C_{12}$-$C_{15}$ benzoate (Finsolv® TN) gave superior results in comparison to those achieved by inclusion of the short chain benzoates (methyl and butyl benzoate). As well as increasing the efficacy of the standard suspension concentrate formulation (Standard SC) of isopyrazam, inclusion of the benzoate adjuvants Benzoflex 181 (2-ethylhexyl benzoate) and Finsolv® TN($C_{12}$-$C_{15}$ benzoate) also resulted in isopyrazam compositions that were better at controlling S. tritici than the standard isopyrazam emulsion concentrate formulation (Standard EC).

TABLE 2

Mean % infection of wheat plants with S. tritici treated with isopyrazam in the presence and absence of benzoic acid ester adjuvants. A standard Tukey HSD test was carried out to assess whether each result was statistically different from the other results and this is expressed as a letter: tests with the same letter are not statistically different ($p < 0.05$).

| Treatment | Mean % infection |
|---|---|
| Standard Isopyrazam SC | 49.4 A |
| Standard Isopyrazam EC | 22.9 B |
| Standard Isopyrazam SC plus Methyl benzoate | 22.1 B |
| Standard Isopyrazam SC plus Butyl benzoate | 18.1 BC |
| Standard Isopyrazam SC plus Benzoflex 181 | 11.4 CD |
| Standard Isopyrazam SC plus Finsolv TN | 5.0 D |

Example 2 Use of Benzoic Acid Ester Adjuvants in Agrochemical Compositions Comprising Epoxyconazole The efficacy of the following benzoic acid esters, methyl benzoate, butyl benzoate, Finsolv® TN ($C_{12}$-$C_{15}$ alkyl benzoate), and Benzoflex 181 (2-ethylhexylbenzoate), as adjuvants in compositions comprising epoxyconazole, was tested and compared to the standard formulation (SC) of the fungicide, which lacks this type of adjuvant.

Wheat plants were inoculated with the fungus Septoria tritici. Four days after inoculation the plants were sprayed with a diluted suspension concentrate formulation of the fungicide epoxyconazole at rates of 3, 10, 30 and 100 mg of the fungicide per liter of spray solution, using a laboratory track sprayer which delivered the spray at a rate of 200 liters per hectare. Spray tests were also carried out with diluted suspension concentrate additionally comprising each of the benzoate adjuvants described above. These adjuvants were added to the spray solution at a rate of 0.2% w/w, based on the quantity of spray liquor. The leaves of the plants were assessed visually 14 days after the spray application and the damage was expressed as the percentage of the leaf area infected. Each spray test was replicated three times across the four application rates and the modelled means of these results are shown in Table 3 below.

TABLE 3

Mean % infection of wheat plants with S. tritici treated with epoxyconazole in the presence and absence of benzoic acid ester adjuvants. A standard Tukey HSD test was carried out to assess whether each result was statistically different from the other results and this is expressed as a letter: tests with the same letter are not statistically different ($p < 0.05$).

| Treatment | Mean % infection |
|---|---|
| Standard epoxyconazole SC | 32.3 B |
| Standard epoxyconazole SC + methyl benzoate | 18.7 C |
| Standard epoxyconazole SC + butyl benzoate | 18.7 C |
| Standard epoxyconazole SC + Finsolv TN | 10.8 CD |
| Standard epoxyconazole SC + Benzoflex 181 | 7.5 D |

The results show that the mean percentage infection with S. tritici is reduced further when the wheat plants were treated with compositions of epoxyconazole comprising each of the benzoates, in comparison to the control (blank) and when treated with the standard SC composition of epoxyconazole. This shows that the benzoates are effective adjuvants for epoxyconazole, and in particular the longer chain alkyl benzoates are more effective than the shorter chain alkyl benzoates.

Example 3 Use of 2-ethylhexyl 4-dimethylaminobenzoate as an Adjuvant for Agrochemical Compositions Comprising Isopyrazam The efficacy of 2-ethylhexyl-4-dimethylamino benzoate as an adjuvant for isopyrazam was tested, and compared to the standard SC and EC formulations which lack this type of adjuvant.

The test was conducted as described above in Example 1, and the modelled means of the results are shown below in Table 4.

TABLE 4

Mean % infection of wheat plants with *S. tritici* treated with isopyrazam in the presence and absence of 2-ethylhexyl 4-dimethylaminobenzoate. A standard Tukey HSD test was carried out to assess whether each result was statistically different from the other results and this is expressed as a letter: tests with the same letter are not statistically different ($p < 0.05$).

| Treatment | Mean infection % |
| --- | --- |
| Standard isopyrazam SC | 47.6 A |
| Standard isopyrazam EC | 19.2 B |
| Standard isopyrazam SC + 2-ethylhexyl 4-dimethylaminobenzoate | 18.2 B |

The inclusion of 2-ethylhexyl 4-dimethylaminobenzoate in compositions of isopyrazam resulted in a reduction *S. tritici* infection in comparison to treatment with the standard SC alone. Thus, 2-ethylhexyl 4-dimethylaminobenzoate is an effective adjuvant for isopyrazam and such compositions are similar in efficacy to the standard EC isopyrazam formulation.

Example 4 Use of 2-ethylhexyl 4-dimethylaminobenzoate as an Adjuvant for Agrochemical Compositions Comprising Epoxyconazole The efficacy of 2-ethylhexyl 4-dimethylamino benzoate as an adjuvant for epoxyconazole was tested, and compared to the standard SC formulation which lacks this type of adjuvant.

The test was conducted as described above in Example 2, and the modelled means of the results are shown below in Table 5. These show that the inclusion of 2-ethylhexyl 4-dimethylaminobenzoate in compositions of epoxyconazole resulted in a reduction *S. tritici* infection in comparison to treatment with the standard SC alone. Thus 2-ethylhexyl-4-dimethylamino benzoate is an effective adjuvant for epoxyconazole.

TABLE 5

Mean % infection of wheat plants with *S. tritici* treated with epoxyconazole in the presence and absence of 2-ethylhexyl-4-dimethylaminobenzoate. A standard Tukey HSD test was carried out to assess whether each result was statistically different from the other results and this is expressed as a letter: tests with the same letter are not statistically different ($p < 0.05$).

| Treatment | Mean infection % |
| --- | --- |
| Standard epoxyconazole SC | 31.1 B |
| Standard epoxyconazole SC + 2-ethylhexyl 4-dimethylaminobenzoate | 7.8 C |

Example 5 Use of a $C_{12}$-$C_{15}$ alkyl Benzoate as an Adjuvant for Agrochemical Compositions Comprising Nicosulfuron The aromatic ester Finsolv® TN ($C_{12}$-$C_{15}$ alkyl benzoate) was tested in a glasshouse against four weed species using the herbicide nicosulfuron. An agrochemical composition was prepared containing 0.2% v/v of the adjuvant in a track sprayer, and was applied at a volume of 200 liters per hectare. Nicosulfuron was applied at either 30 or 60 grams of pesticide per hectare on each of the weed species. The weed species and their growth stage at spraying were *Abutilon theophrasti* (ABUTH; growth stage 13), *Chenopodium album* (CHEAL; growth stage 14), *Digitaria sanguinalis* (DIGSA; growth stage 13), and *Setaria viridis* (SETVI; growth stage 13).

Each spray test replicated three times. The efficacy of the herbicide was assessed visually and expressed as a percentage of the leaf area killed. Samples were assessed at time periods of 7, 14 and 20 days following application. The results shown in Table 6 below are mean averages over the two rates of nicosulfuron, three replicates and the three assessment timings, and are compared to the efficacy of nicosulfuron in the absence of an adjuvant, and nicosulfuron in the presence of the commercially available tank-mix adjuvant, Atplus411F®.

A second experiment was conducted to assess the efficacy of Finsolv® TN as an adjuvant in compositions of nicosulfuron. This was carried out as outlined above, with the following change: samples were assessed at 14 and 20 days post application.

The results shown in Table 7 below are mean averages over the two rates of nicosulfuron, three replicates and the two assessment timings, and are compared to the efficacy of nicosulfuron in the absence of an adjuvant, and nicosulfuron in the presence of the commercially available tank-mix adjuvant, Atplus411F®.

TABLE 6

Mean percentage kill results for nicolsulfuron in the presence and absence of Finsolv ®TN and Atplus 411F ®. A standard Tukey HSD test was carried out to assess whether each result was statistically different from the other results and this is expressed as a letter: tests with the same letter are not statistically different ($p < 0.05$).

| Treatment | SETVI | DIGSA | CHEAL | ABUTH | Mean across species |
| --- | --- | --- | --- | --- | --- |
| Nicosulfuron + FINSOLV TN | 50.6 A | 50 A | 40.0 A | 26.1 AB | 41.7 A |
| Nicosulfuron + | 41.8 B | 43 A | 43.9 A | 30.0 A | 39.6 A |

TABLE 6-continued

Mean percentage kill results for nicolsulfuron in the presence
and absence of Finsolv ®TN and Atplus 411F ®.
A standard Tukey HSD test was carried out to assess whether
each result was statistically different from the other results
and this is expressed as a letter: tests with the same letter
are not statistically different ($p < 0.05$).

| Treatment | SETVI | DIGSA | CHEAL | ABUTH | Mean across species |
|---|---|---|---|---|---|
| ATPLUS 411 F |  |  |  |  |  |
| Nicosulfuron | 33.3 C | 1.1 B | 26.7 B | 19.4 B | 20.1 B |

TABLE 7

Mean percentage kill results for nicolsulfuron in the presence
and absence of Finsolv ®TN and Atplus 411F ®.
A standard Tukey HSD test was carried out to assess whether
each result was statistically different from the other results
and this is expressed as a letter: tests with the same letter
are not statistically different ($p < 0.05$).

| Treatment | ABUTH | CHEAL | DIGSA | SETVI | Mean across species |
|---|---|---|---|---|---|
| Nicosulfuron + FINSOLV TN | 41.7 A | 77.9 A | 85.6 A | 88.2 A | 72.1 A |
| Nicosulfuron + ATPLUS 411 F | 43.8 A | 75.4 A | 80.2 A | 80.0 B | 69.8 A |
| Nicosulfuron | 29.2 B | 25.8 B | 0.0 B | 61.3 C | 29.1 B |

Both experiments show that the $C_{12}$-$C_{15}$ benzoate is an effective adjuvant (with comparable efficacy to the commercially available tank-mix adjuvant Atplus411F®) for nicosulfuron.

Example 6 Use of a $C_{12}$-$C_{15}$ alkyl Benzoate as an Aduvant for Agrochemical Compositions Comprising Fomesafen The aromatic ester Finsolv® TN ($C_{12}$-$C_{15}$ alkyl benzoate) was tested in a glasshouse against four weed species using the herbicide fomesafen. An agrochemical composition was prepared containing 0.2% v/v of the adjuvant in a track sprayer and was applied at a volume of 200 liters per hectare. Fomesafen was applied at either 60 or 120 grams of pesticide per hectare on each of the weed species. The weed species and their growth stage at spraying were *Chenopodium album* (CHEAL; growth stage 14), *Abutilon theophrasti* (ABUTH; growth stage 12), *Setaria viridis* (SETVI; growth stage 13), and *Xanthium strumarium* (XANST; growth stage 12).

Each spray test was replicated three times. The efficacy of the herbicide was assessed visually and expressed as a percentage of the leaf area killed. Samples were assessed at time periods of 7, 14 and 20 days following application. The results shown in Table 8 below are mean averages over the two rates of fomesafen, three replicates and the three assessment timings, and are compared to the efficacy of fomesafen in the absence of an adjuvant, and fomesafen in the presence of the commercially available adjuvant Turbocharge®.

TABLE 8

Mean percentage kill results for fomesafen in the presence and absence
of Finsolv ®TN and Turbocharge ®. A standard Tukey HSD
test was carried out to assess whether each result was statistically
different from the other results and this is expressed as a letter:
tests with the same letter are not statistically different ($p < 0.05$).

| Treatment | ABUTH | CHEAL | SETVI | XANST | Mean across species |
|---|---|---|---|---|---|
| Fomesafen + Turbocharge ® | 82.9 A | 75 A | 22.8 A | 94.1 A | 68.7 A |
| Fomesafen + FINSOLV ® TN | 60.6 B | 63.1 B | 22.2 A | 84.4 B | 57.6 B |
| Fomesafen | 19.7 C | 34.7 C | 10.3 B | 59.2 C | 31.0 C |

A second experiment was conducted to assess the efficacy of Finsolv® TN as an adjuvant in compositions of fomesafen. This was carried out as outlined above, with the following change: samples were assessed at 6, 14 and 20 days post application.

The results shown in Table 9 below are mean averages over the two rates of fomesafen, three replicates, three assessment timings, and four weed species and are compared to the efficacy of fomesafen in the absence of an adjuvant, and fomesafen in the presence of the commercially available tank-mix adjuvant, Turbocharge®.

TABLE 9

Mean percentage kill results for fomesafen in the presence and absence
of Finsolv ®TN or Turbocharge ®. A standard Tukey HSD
test was carried out to assess whether each result was statistically
different from the other results and this is expressed as a letter:
tests with the same letter are not statistically different ($p < 0.05$).

| Treatment | Mean across species |
|---|---|
| Fomesafen + Turbocharge ® | 73.8 A |
| Fomesafen + FINSOLV ®TN | 70.5 A |
| Fomesafen | 44.9 B |

The results show that the $C_{12}$-$C_{15}$ alkyl benzoate is an effective adjuvant for fomesafen.

Example 7 Use of a $C_{12}$-$C_{15}$ alkyl Benzoate as an Aduvant for Agrochemical Compositions Comprising Mesotrione The aromatic ester Finsolv® TN ($C_{12}$-$C_{15}$ alkyl benzoate) was tested in a glasshouse against three weed species using the herbicide mesotrione. An agrochemical composition was prepared containing 0.2% v/v of the adjuvant in a track sprayer and was applied at a volume of 200 liters per hectare. Mesotrione was applied at either 60 or 120 grams of pesticide per hectare on weeds which had been grown to the 1.3 or 1.4 leaf stage. The weed species were *Xanthium strumarium* (XANST), *Brachiaria platyphylla* (BRAPL), and *Digitaria sanguinalis* (DIGSA). The commercially available surfactant Tetronic® 1107 was used in the spray tank at a concentration of 0.036 g/l alongside the lower concentration of mesotrione and at a concentration of 0.072 g/l at the higher concentration of mesotrione.

Each spray test was replicated three times. The efficacy of the herbicide was assessed visually and expressed as a percentage of the leaf area killed. Samples were assessed at time periods of 7, 14 and 20 days following application. The results shown in Table 10 below are mean averages over the two rates of mesotrione, three replicates and the three assessment timings, and are compared to the efficacy of mesotrione in the absence of adjuvant and mesotrione in the presence of the well-known adjuvant Tween® 20.

TABLE 10

Mean percentage kill results for mesotrione in the presence and absence of Finsolv® TN or Tween® 20. A standard Tukey HSD test was carried out to assess whether each result was statistically different from the other results and this is expressed as a letter: tests with the same letter are not statistically different (p < 0.05).

| Adjuvant | BRAPL | DIGSA | XANST | Mean across species |
|---|---|---|---|---|
| Mesotrione + FINSOLV ®TN | 24.7 A | 37.2 A | 36.7 A | 33.6 A |
| Mesotrione + Tween ® 20 | 18.3 A | 35.6 A | 41.7 A | 31.9 A |
| Mesotrione | 5.3 B | 20.0 B | 36.7 A | 19.9 B |

A second experiment was conducted to assess the efficacy of Finsolv® TN as an adjuvant in compositions of mesotrione. This was carried out as outlined above, with the following change: samples were assessed at 6, 14 and 20 days post application.

The results shown in Table 11 below are mean averages over the two rates of mesotrione, three replicates, the three assessment timings, and the three weed species, and are compared to the efficacy of mesotrione in the absence of adjuvant and mesotrione in the presence of the well-known adjuvant Tween® 20.

TABLE 11

Mean percentage kill results for mesotrione in the presence and absence of Finsolv ® TN or Tween ® 20. A standard Tukey HSD test was carried out to assess whether each result was statistically different from the other results and this is expressed as a letter: tests with the same letter are not statistically different (p < 0.05).

| Treatment | Mean across species |
|---|---|
| Mesotrione + FINSOLV ® TN | 57.4 A |
| Mesotrione + Tween ® 20 | 55.5 A |
| Mesotrione | 33.0 B |

The results of both experiments show that the $C_{12}$-$C_{15}$ benzoate is an effective adjuvant for mesotrione, and is as efficacious as the known adjuvant Tween®20.

Example 8 Use of a $C_{12}$-$C_{15}$ alkyl Benzoate as an Aduvant for Agrochemical Compositions Comprising Pinoxaden The aromatic ester Finsolv® TN ($C_{12}$-$C_{15}$ alkyl benzoate) was tested in a glasshouse against four weed species using the herbicide pinoxaden. An agrochemical composition was prepared containing 0.2% v/v of the adjuvant in a track sprayer and was applied at a volume of 200 liters per hectare. Pinoxaden was applied at either 7.5 or 15 grams of pesticide per hectare on each of the weed species. The commercially available surfactant Atlas® G5000 was used in the spray tank at a concentration of 0.00375 g/l alongside the lower concentration of pinoxaden and at a concentration of 0.0075 g/l at the higher concentration of pinoxaden. The weed species and their growth stage at spraying were *Alopecurus myosuroides* (ALOMY; growth stage 13), *Avena fatua* (AVEFA; growth stage 12); *Lolium perenne* (LOLPE; growth stage 13), *Setaria viridis* (SETVI; growth stage 14).

Each spray test was replicated three times. The efficacy of the herbicide was assessed visually and expressed as a percentage of the leaf area killed. Samples were assessed at time periods of 7, 14 and 20 days following application. The results shown in Table 12 below are mean averages over the two rates of pinoxaden, three replicates and the three assessment timings, and are compared to the efficacy of pinoxaden in the absence of an adjuvant and pinoxaden in the presence of triethylhexyl phosphate.

TABLE 12

Mean percentage kill results for pinoxaden in the presence and absence of Finsolv ®TN or Tween ®20. A standard Tukey HSD test was carried out to assess whether each result was statistically different from the other results and this is expressed as a letter: tests with the same letter are not statistically different (p < 0.05).

| Treatment | ALOMY | AVEFA | LOLPE | SETVI | Mean across species |
|---|---|---|---|---|---|
| Pinoxaden + FINSOLV ®TN | 6.1 AB | 70.1 A | 53.3 A | 68.2 A | 49.43 A |
| Pinoxaden + Triethylhexyl phosphate | 7.8 A | 66.2 A | 55.3 A | 71.4 A | 50.17 A |
| Pinoxaden | 1.1 B | 2.8 B | 5.0 B | 0.8 B | 2.43 B |

A second experiment was conducted to assess the efficacy of Finsolv® TN as an adjuvant for pinoxaden. This was carried out as outlined above, with the following change: samples were assessed at 14 and 20 days post application. The results shown below in Table 13 are mean averages over the two rates of pinoxaden, three replicates, the two assessment timings, and the four weed species, and are compared to the efficacy of pinoxaden in the absence of an adjuvant and pinoxaden in the presence of the common adjuvant methyl oleate.

Both experiments show that the $C_{12}$-$C_{15}$ alky benzoate is an effective adjuvant for pinoxaden, and is at least as efficacious as compounds known to be useful as adjuvants in the agrochemical arena.

TABLE 13

Mean percentage kill results for pinoxaden in the presence and absence of Finsolv ®TN or methyl oleate. A standard Tukey HSD test was carried out to assess whether each result was statistically different from the other results and this is expressed as a letter: tests with the same letter are not statistically different (p < 0.05).

| Treatment | Mean across species |
|---|---|
| Pinoxaden + FINSOLV ®TN | 87.0 A |
| Pinoxaden + methyl oleate | 82.3 A |
| Pinoxaden | 0.5 B |

Example 9 Synthesis of a $C_{16}$-$C_{17}$ benzoic acid ester: "Benzoate 1"

The adjuvant mixture "Benzoate 1" was synthesised by adding an oil comprising a mixture of linear long chain (16 and 17 carbons in length) alcohols to a flask and reacting this oil with benzoyl chloride. The resulting mixture was extracted after the reaction and purified. Analysis by nmr showed that the product consisted of long-chain (16 and 17 carbons in length) benzoates. This benzoic acid ester was tested as an adjuvant in Examples 10, 11, 12, and 13 described supra.

Example 10 Use of Benzoic Acid Ester Adjuvants in Agrochemical Compositions Comprising Nicosulfuron The aromatic esters Benzoate 1 (see Example 9), Benzoflex 354 (2,2,4-trimethyl-1,3-pentanediol dibenzoate) and Finsolv® SB (stearyl benzoate) were tested in a glasshouse against four weed species using the herbicide nicosulfuron. Nicosulfuron was applied at either 30 or 60 grams of pesticide per hectare on each of the weed species. The weed species and their growth stage at spraying were *Abutilon theophrasti* (ABUTH; growth stage 13), *Chenopodium album* (CHEAL; growth stage 14), *Digitaria sanguinalis* (DIGSA; growth stage 13), and *Setaria viridis* (SETVI; growth stage 13).

Each spray test replicated three times. The efficacy of the herbicide was assessed visually and expressed as a percentage of the leaf area killed. Samples were assessed at time periods of 14 and 20 days following application. The results shown in Table 14 below are mean averages over the two rates of nicosulfuron, three replicates and the two assessment timings, and are compared to the efficacy of nicosulfuron in the absence of an adjuvant, and nicosulfuron in the presence of the commercially available tank-mix adjuvant, Atplus411F®.

TABLE 14

Mean percentage kill results for nicosulfuron in the presence and absence of Benzoate 1, Finsolv ®SB, Benzoflex 354 or Atplus 411F ®. A standard Tukey HSD test was carried out to assess whether each result was statistically different from the other results and this is expressed as a letter: tests with the same letter are not statistically different (p < 0.05).

| Treatment | Mean across species | SETVI | ABUTH | CHEAL | DIGSA |
|---|---|---|---|---|---|
| Nicosulfuron + BENZOATE 1 | 75.9 A | 89.7 A | 65.4 B | 59.2 A | 89.3 A |
| Nicosulfuron + BENZOFLEX 354 | 75.9 A | 88.6 A | 72.1 A | 59.6 A | 83.2 A |
| Nicosulfuron + FINSOLV ®SB | 75.1 A | 89.9 A | 62.9 B | 59.6 A | 87.9 A |
| Nicosulfuron + ATPLUS 411 F ® | 74.3 A | 89.2 A | 63.8 B | 60.0 A | 84.3 A |
| Nicosulfuron | 59.6 B | 81.0 B | 56.7 C | 44.6 B | 56.3 B |

The results show that each of the benzoic acid ester is effective as an adjuvant for nicosulfruon.

Example 11 Use of Benzoic Acid Ester Adjuvants in Agrochemical Compositions Comprising Fomesafen The aromatic esters Benzoate 1 (see Example 9),), Benzoflex 354 (2,2,4-trimethyl-1,3-pentanediol dibenzoate) and Finsolv® SB (stearyl benzoate) were tested in a glasshouse against four weed species using the herbicide fomesafen.

An agrochemical composition was prepared containing 0.2% v/v of the adjuvant in a track sprayer and was applied at a volume of 200 liters per hectare. Fomesafen was applied at either 60 or 120 grams of pesticide per hectare on each of the weed species. The weed species and their growth stage at spraying were *Chenopodium album* (CHEAL; growth stage 14), *Abutilon theophrasti* (ABUTH; growth stage 12), *Setaria viridis* (SETVI; growth stage 13), and *Xanthium strumarium* (XANST; growth stage 12).

Each spray test was replicated three times. The efficacy of the herbicide was assessed visually and expressed as a percentage of the leaf area killed. Samples were assessed at time periods of 7, 14 and 20 days following application. The results shown in Table 15 below are mean averages over the two rates of fomesafen, three replicates the three assessment timings, and the four weed species, and are compared to the efficacy of fomesafen in the absence of an adjuvant, and fomesafen in the presence of the commercially available adjuvant Turbocharge®.

TABLE 15

Mean percentage kill results for fomesafen in the presence and absence of benzoate 1, benzoflex 354, Finsolv ®SB or Turbocharge ®. A standard Tukey HSD test was carried out to assess whether each result was statistically different from the other results and this is expressed as a letter: tests with the same letter are not statistically different (p < 0.05).

| Treatment | Mean across species |
|---|---|
| Fomesafen + FINSOLV SB | 58.9 A |
| Fomesafent + BENZOATE 1 | 58.5 A |
| Fomesafen + Turbocharge (R) | 58.5 A |
| Fomesafe + BENZOFLEX 354 | 43.9 B |
| Fomesafen | 37.7 C |

The results demonstrate that all of the benzoic acid esters tested are effective as adjuvants for fomesafen and that isostearyl benzoate, and the $C_{16}$-$C_{17}$ alkyl benzoate (benzoate 1) are as effective as the commercially available agrochemical adjuvant Turbocharge®.

Example 12 Use of Benzoic Acid Ester Adjuvants in Agrochemical Compositions Comprising Mesotrione The aromatic esters benzoate 1 (see Example 9), Benzoflex 354 (2,2,4-trimethyl-1,3-pentanediol dibenzoate) and Finsolv® SB (stearyl benzoate) were tested in a glasshouse against three weed species using the herbicide mesotrione.

An agrochemical composition was prepared containing 0.2% v/v of the adjuvant in a track sprayer and was applied at a volume of 200 liters per hectare. Mesotrione was applied at either 60 or 120 grams of pesticide per hectare on weeds which had been grown to the 1.3 or 1.4 leaf stage. The weed species were *Xanthium strumarium* (XANST), *Brachiaria platyphylla* (BRAPL), and *Digitaria sanguinalis* (DIGSA). The commercially available surfactant Tetronic® 1107 was used in the spray tank at a concentration of 0.036 g/l alongside the lower concentration of mesotrione and at a concentration of 0.072 g/l at the higher concentration of mesotrione.

Each spray test was replicated three times. The efficacy of the herbicide was assessed visually and expressed as a percentage of the leaf area killed. Samples were assessed at time periods of 7, 14 and 20 days following application. The results shown in Table 10 below are mean averages over the two rates of mesotrione, three replicates and the three assessment timings, and are compared to the efficacy of mesotrione in the absence of adjuvant and mesotrione in the presence of the well-known adjuvant Brij®96. The results shown in Table 16 below are mean averages over the two rates of mesotrione, three replicates, three assessment timings and three weed species. The results are compared to the efficacy of mesotrione in the absence of an adjuvant and mesotrione in the presence of the commercially available adjuvant Brij®96.

TABLE 16

Mean percentage kill results for mesotrione in the presence and absence of benzoate 1, Benzoflex 354, Finsolv ®SB (stearyl benzoate) or Brij ®96. A standard Tukey HSD test was carried out to assess whether each result was statistically different from the other results and this is expressed as a letter: tests with the same letter are not statistically different ($p < 0.05$).

| Treatment | Mean across species |
| --- | --- |
| Mesotrione + BENZOATE 1 | 45.5 A |
| Mesotrione + FINSOLV ®SB | 42.5 AB |
| Mesotrione + BRIJ ®96 | 40.1 B |
| Mesotrione + BENZOFLEX 354 | 36.4 B |
| Mesotrione | 18.0 C |

The results show that all of the benzoic acid esters are effective adjuvants for mesotrione, and that benzoate 1 and Finsolv® SB (i.e. the longer chain alkyl benzoates) are particularly effective.

Example 13 Use of Benzoic Acid Ester Adjuvants in Agrochemical Compositions Comprising Pinoxaden The aromatic esters benzoate 1 (see Example 9), Benzoflex 354 (2,2,4-trimethyl-1,3-pentanediol dibenzoate) and Finsolv® SB (stearyl benzoate) were tested in a glasshouse against four weed species using the herbicide pinoxaden.

An agrochemical composition was prepared containing 0.2% v/v of the adjuvant in a track sprayer and was applied at a volume of 200 liters per hectare. Pinoxaden was applied at either 7.5 or 15 grams of pesticide per hectare on each of the weed species. The commercially available surfactant Atlas® G5000 was used in the spray tank at a concentration of 0.00375 g/l alongside the lower concentration of pinoxaden and at a concentration of 0.0075 g/l at the higher concentration of pinoxaden. The weed species and their growth stage at spraying were *Alopecurus myosuroides* (ALOMY; growth stage 13), *Avena fatua* (AVEFA; growth stage 12); *Lolium perenne* (LOLPE; growth stage 13), *Setaria viridis* (SETVI; growth stage 14).

Each spray test was replicated three times. The efficacy of the herbicide was assessed visually and expressed as a percentage of the leaf area killed. Samples were assessed at time periods of 7, 14 and 20 days following application. The results shown in Table 17 below are mean averages over the two rates of pinoxaden, three replicates and the three assessment timings, and are compared to the efficacy of pinoxaden in the absence of an adjuvant and pinoxaden in the presence of Brij®96.

The results show that each of the benzoic acid esters tested is an effective adjuvant for pinoxaden, and that benzoate 1 and Finsolv® SB (i.e. the longer chain alkyl benzoates) are particularly effective.

TABLE 17

Mean percentage kill results for pinoxaden in the presence and absence of benzoate 1, Benzoflex 354, Finsolv ®SB (stearyl benzoate) or Brij ®96. A standard Tukey HSD test was carried out to assess whether each result was statistically different from the other results and this is expressed as a letter: tests with the same letter are not statistically different ($p < 0.05$)..

| Treatment | Mean across species |
| --- | --- |
| Pinoxaden + BENZOATE 1 | 57.7 A |
| Pinoxaden + FINSOLV ® SB | 54.3 A |
| Pinoxaden + BRIJ ®96 | 49.7 A |
| Pinoxaden + BENZOFLEX 354 | 36.4 B |
| Pinoxaden | 1.8 C |

Example 14 Use of Benzoic Acid Ester Adjuvants in Agrochemical Compositions Comprising Pinoxaden The aromatic esters Finsolv® SB (stearyl benzoate), Finsolv® TN and the aromatic ester ethoxylate Dermol 25-3B were tested in a glasshouse against four weed species using the herbicide pinoxaden.

An agrochemical composition was prepared containing 0.2% v/v of the adjuvant in a track sprayer and was applied at a volume of 200 liters per hectare. The adjuvant oils were emulsified using a small amount of the surfactant Pluronic® PE 10500, which was present in the composition at a concentration of 0.02% v/v. Pinoxaden was applied at either 7.5 or 15 grams of pesticide per hectare on each of the weed species. The commercially available surfactant Atlas® G5000 was used in the spray tank at a concentration of 0.00375 g/l alongside the lower concentration of pinoxaden and at a concentration of 0.0075 g/l at the higher concentration of pinoxaden. The weed species and their growth stage at spraying were *Alopecurus myosuroides* (ALOMY; growth stage 13), *Avena fatua* (AVEFA; growth stage 12); *Lolium perenne* (LOLPE; growth stage 13), *Setaria viridis* (SETVI; growth stage 13-14).

Each spray test was replicated three times. The efficacy of the herbicide was assessed visually and expressed as a percentage of the leaf area killed. Samples were assessed at time periods of 14 and 21 days following application. The results shown in Table 18 below are mean averages over the two rates of pinoxaden, three replicates and the two assessment timings, and are compared to the efficacy of pinoxaden in the absence of an adjuvant and pinoxaden in the presence of tris 2ethylhexylphosphate (TEHP).

The results show that each of the benzoic acid esters tested is an effective adjuvant for pinoxaden, and that Dermot® 25-3B was particularly effective.

TABLE 18

Mean percentage kill results for pinoxaden in the presence and absence of Finsolv ®SB, Finsolv ®TN and the aromatic ester ethoxylate Dermol 25-3B or Atplus 411F ®. A standard Tukey HSD test was carried out to assess whether each result was statistically different from the other results and this is expressed as a letter: tests with the same letter are not statistically different ($p < 0.05$)..

| Treatment | Mean across species |
| --- | --- |
| Pinoxaden + Dermol 25-3B | 77.7A |
| Pinoxaden + TEHP | 75.7A |
| Pinoxaden + Finsolv SB | 74.4A |
| Pinoxaden + Finsolv TN | 72.4A |
| Pinoxaden | 2.6B |

Example 15 Use of Benzoic Acid Ester Adjuvants in Agrochemical Compositions Comprising Nicosulfuron The aromatic esters Finsolv® SB (stearyl benzoate), Finsolv® TN and the aromatic ester ethoxylate Dermol 25-3B were tested in a glasshouse against four weed species using the herbicide nicosulfuron.

An agrochemical composition was prepared containing 0.2% v/v of the adjuvant in a track sprayer and was applied at a volume of 200 liters per hectare. The adjuvant oils were emulsified using a small amount of the surfactant Pluronic® PE 10500, which was present in the composition at a concentration of 0.02% v/v. Nicosulfuron was applied at either 30 or 60 grams of pesticide per hectare on each of the weed species. The weed species and their growth stage at spraying were *Abutilon theophrasti* (ABUTH; growth stage 13), *Chenopodium album* (CHEAL; growth stage 14-15), *Digitaria sanguinalis* (DIGSA; growth stage 14), and *Setaria viridis* (SETVI; growth stage 13-14).

Each spray test replicated three times. The efficacy of the herbicide was assessed visually and expressed as a percentage of the leaf area killed. Samples were assessed at time periods of 14 and 21 days following application. The results shown in Table 19 below are mean averages over the two rates of nicosulfuron, three replicates and the two assessment timings, and are compared to the efficacy of nicosulfuron in the absence of an adjuvant, and nicosulfuron in the presence of the commercially available tank-mix adjuvant, Atplus411F®.

TABLE 19

Mean percentage kill results for nicosulfuron in the presence and absence of Finsolv ®SB (stearyl benzoate), Finsolv ®TN and the aromatic ester ethoxylate Dermol 25-3B. A standard Tukey HSD test was carried out to assess whether each result was statistically different from the other results and this is expressed as a letter: tests with the same letter are not statistically different ($p < 0.05$).

| Treatment | Mean across species |
| --- | --- |
| Nicosulfuron + Dermol ® 25-3B | 67.5A |
| Nicosulfuron + Finsolv ®SB | 66.6A |
| Nicosulfuron + FINSOLV ®TN | 66A |
| Nicosulfuron + ATPLUS 411 F ® | 60.9A |
| Nicosulfuron | 29.8B |

The results show that each of the benzoic acid ester is effective as an adjuvant for nicosulfruon.

Example 16 Use of Benzoic Acid Ester Adjuvants in Agrochemical Compositions Comprising Fomesafen The aromatic esters Finsolv® SB (stearyl benzoate), Finsolv® TN and the aromatic ester ethoxylate Dermol 25-3B were tested in a glasshouse against four weed species using the herbicide fomesafen.

An agrochemical composition was prepared containing 0.2% v/v of the adjuvant in a track sprayer and was applied at a volume of 200 liters per hectare. The adjuvant oils were emulsified using a small amount of the surfactant Pluronic® PE 10500, which was present in the composition at a concentration of 0.02% v/v. Fomesafen was applied at either 60 or 120 grams of pesticide per hectare on each of the weed species. The weed species and their growth stage at spraying were *Polygonum convolvulus* (POLCO; growth stage 13-14), *Brachiaria plantaginea* (BRAL; growth stage 13-14), *Digitaria sanguinalis* (DIGSA; growth stage 14), and *Commelina benghalensis* (COMBE; growth stage 13-14).

Each spray test was replicated three times. The efficacy of the herbicide was assessed visually and expressed as a percentage of the leaf area killed. Samples were assessed at time periods of 14 and 21 days following application. The results shown in Table 20 below are mean averages over the two rates of fomesafen, three replicates the two assessment timings, and the four weed species, and are compared to the efficacy of fomesafen in the absence of an adjuvant, and fomesafen in the presence of the commercially available adjuvant Turbocharge®.

TABLE 20

Mean percentage kill results for fomesafen in the presence and absence of Finsolv ®SB (stearyl benzoate), Finsolv ®TN and the aromatic ester ethoxylate Dermol 25-3B or Turbocharge ®. A standard Tukey HSD test was carried out to assess whether each result was statistically different from the other results and this is expressed as a letter: tests with the same letter are not statistically different ($p < 0.05$).

| Treatment | Mean across species |
| --- | --- |
| Fomesafen + Dermol 25-3B | 61.7A |
| Fomesafen + Turbocharge | 60.7AB |
| Fomesafen + Finsolv SB | 55.8B |
| Fomesafe + Finsolv TN | 45.4C |
| Fomesafen | 24.3D |

The results demonstrate that all of the benzoic acid esters tested are effective as adjuvants for fomesafen and that Finsolv SB and Dermol 25-3B are as effective as the commercially available agrochemical adjuvant Turbocharge®.

Example 17 Use of Benzoic Acid Ester Adjuvants in Agrochemical Compositions Comprising Mesotrione The aromatic esters Finsolv® SB (stearyl benzoate), Finsolv® TN and the aromatic ester ethoxylate Dermol 25-3B were tested in a glasshouse against three weed species using the herbicide mesotrione.

An agrochemical composition was prepared containing 0.2% v/v of the adjuvant in a track sprayer and was applied at a volume of 200 liters per hectare. The adjuvant oils were emulsified using a small amount of the surfactant Pluronic® PE 10500, which was present in the composition at a concentration of 0.02% v/v. Mesotrione was applied at either 60 or 120 grams of pesticide per hectare on weeds which had been grown to the 1.3 or 1.4 leaf stage. The weed species were *Xanthium strumarium* (XANST), *Brachiaria platyphylla* (BRAPL), and *Digitaria sanguinalis* (DIGSA). The commercially available surfactant Tetronic® 1107 was used in the spray tank at a concentration of 0.036 g/l alongside the lower concentration of mesotrione and at a concentration of 0.072 g/l at the higher concentration of mesotrione.

Each spray test was replicated three times. The efficacy of the herbicide was assessed visually and expressed as a percentage of the leaf area killed. Samples were assessed at time periods of 14 and 21 days following application. The results shown in Table 10 below are mean averages over the two rates of mesotrione, three replicates and the two assessment timings, and are compared to the efficacy of mesotrione in the absence of adjuvant and mesotrione in the presence of the well-known adjuvant Tween®20. The results shown in Table 16 below are mean averages over the two rates of mesotrione, three replicates, three assessment timings and three weed species. The results are compared to the efficacy of mesotrione in the absence of an adjuvant and mesotrione in the presence of the commercially available adjuvant Tween®20.

TABLE 21

Mean percentage kill results for mesotrione in the presence and absence of Finsolv ®SB (stearyl benzoate), Finsolv ®TN and the aromatic ester ethoxylate Dermol ®25-3B or Tween ®20. A standard Tukey HSD test was carried out to assess whether each result was statistically different from the other results and this is expressed as a letter: tests with the same letter are not statistically different ($p < 0.05$).

| Treatment | Mean across species |
| --- | --- |
| Mesotrione + Tween ® 20 | 43.4A |
| Mesotrione + Dermol ®25-3B | 42A |
| Mesotrione + FINSOLV ®SB | 38.3A |
| Mesotrione + FINSOLV ®TN | 32.7B |
| Mesotrione | 19.9C |

The results show that all of the benzoic acid esters are effective adjuvants for mesotrione, and that Dermol®25-3B and Finsolv® SB (i.e. the longer chain alkyl benzoates) are particularly effective.

Example 18 Use of Benzoic Acid Ester Adjuvants in Agrochemical Compositions Comprising Pinoxaden The aromatic esters Finsolv® TN and the aromatic ester ethoxylate Dermol 25-3B were tested in a glasshouse against four weed species using the herbicide pinoxaden. An agrochemical composition was prepared containing either 0.2, 0.1, 0.05 or 0.025% v/v of the adjuvant in a track sprayer and was applied at a volume of 200 liters per hectare. The adjuvant tris(2-ethylhexyl) phosphate was applied at 0.5% v/v. An agrochemical composition was prepared containing 0.2% v/v of the adjuvant in a track sprayer and was applied at a volume of 200 liters per hectare. Pinoxaden was applied at either 7.5 or 15 grams of pesticide per hectare on each of the weed species. The commercially available surfactant Atlas® G5000 was used in the spray tank at a concentration of 0.00375 g/l alongside the lower concentration of pinoxaden and at a concentration of 0.0075 g/l at the higher concentration of pinoxaden.

The weed species and their growth stage at spraying were *Alopecurus myosuroides* (ALOMY; growth stage 21), *Avena fatua* (AVEFA; growth stage 12); *Lolium perenne* (LOLPE; growth stage 13), *Setaria viridis* (SETVI; growth stage 12).

Each spray test was replicated three times. The efficacy of the herbicide was assessed visually and expressed as a percentage of the leaf area killed. Samples were assessed at time periods of 14 and 21 days following application. The results shown in Table 22 below are mean averages over the two rates of pinoxaden, three replicates and the two assessment timings, and are compared to the efficacy of pinoxaden in the absence of an adjuvant and pinoxaden in the presence of tris(2-ethylhexyl) phosphate.

The results show that each of the benzoic acid esters tested is an effective adjuvant for pinoxaden, and that Dermol® 25-3B was particularly effective.

TABLE 22

Mean percentage kill results for pinoxaden in the presence and absence of Finsolv ®TN and the aromatic ester ethoxylate Dermol 25-3B or Atplus 411F ®. A standard Tukey HSD test was carried out to assess whether each result was statistically different from the other results and this is expressed as a letter: tests with the same letter are not statistically different ($p < 0.05$)..

| Treatment | Adjuvant rate % v/v | Mean across species |
| --- | --- | --- |
| Pinoxaden + FINSOLV ®TN | 0.1 | 87A |
| Pinoxaden + Dermol ® 25-3B | 0.1 | 86.5A |
| Pinoxaden + Dermol ® 25-3B | 0.2 | 86.3A |
| Pinoxaden + ATPLUS 411 F ® | 0.5 | 86.1AB |
| Pinoxaden + FINSOLV ®TN | 0.2 | 86AB |
| Pinoxaden + Dermol ® 25-3B | 0.05 | 81.6AB |
| Pinoxaden + FINSOLV ®TN | 0.05 | 79.1BC |
| Pinoxaden + Dermol ® 25-3B | 0.025 | 72.9CD |
| Pinoxaden + FINSOLV ®TN | 0.025 | 69.2D |
| Pinoxaden | | 3.6E |

Example 19 Use of Benzoic Acid Ester Adjuvants in Agrochemical Compositions Comprising Nicosulfuron The aromatic ester Finsolv® TN and the aromatic ester ethoxylate Dermol® 25-3B were tested in a glasshouse against four weed species using the herbicide nicosulfuron. An agrochemical composition was prepared containing either 0.2, 0.1, 0.05 or 0.025% v/v of the adjuvant in a track sprayer and was applied at a volume of 200 liters per hectare. The commercial adjuvant Atplus®411F was applied at 0.5% v/v. Nicosulfuron was applied at either 30 or 60 grams of pesticide per hectare on each of the weed species. The weed species and their growth stage at spraying were *Abutilon theophrasti* (ABUTH; growth stage 11-12), *Chenopodium album* (CHEAL; growth stage 13-15), *Digitaria sanguinalis* (DIGSA; growth stage 13-21), and *Setaria viridis* (SETVI; growth stage 13).

Each spray test replicated three times. The efficacy of the herbicide was assessed visually and expressed as a percentage of the leaf area killed. Samples were assessed at time periods of 14 and 21 days following application. The results shown in Table 23 below are mean averages over the two rates of nicosulfuron, three replicates and the two assessment timings, and are compared to the efficacy of nicosulfuron in the absence of an adjuvant, and nicosulfuron in the presence of the commercially available tank-mix adjuvant, Atplus411F®.

TABLE 23

Mean percentage kill results for nicosulfuron in the presence and absence of Finsolv ®TN and the aromatic ester ethoxylate Dermol ®25-3B. A standard Tukey HSD test was carried out to assess whether each result was statistically different from the other results and this is expressed as a letter: tests with the same letter are not statistically different ($p < 0.05$).

| Treatment | Adjuvant rate % v/v | Mean across species |
| --- | --- | --- |
| Nicosulfuron + Dermol ® 25-3B | 0.1 | 64.4A |
| Nicosulfuron + Dermol ® 25-3B | 0.2 | 65A |
| Nicosulfuron + ATPLUS 411 F ® | 0.5 | 63.1A |
| Nicosulfuron + FINSOLV ®TN | 0.2 | 62.8A |
| Nicosulfuron + FINSOLV ®TN | 0.1 | 60.5AB |
| Nicosulfuron + Dermol ® 25-3B | 0.05 | 59.4AB |
| Nicosulfuron + FINSOLV ®TN | 0.05 | 55.6BC |
| Nicosulfuron + FINSOLV ®TN | 0.025 | 54.8BC |

TABLE 23-continued

Mean percentage kill results for nicosulfuron in the presence
and absence of Finsolv ®TN and the aromatic ester ethoxylate
Dermol ®25-3B. A standard Tukey HSD test was carried out
to assess whether each result was statistically different from
the other results and this is expressed as a letter: tests with
the same letter are not statistically different (p < 0.05).

| Treatment | Adjuvant rate % v/v | Mean across species |
|---|---|---|
| Nicosulfuron + Dermol ® 25-3B | 0.025 | 50.7C |
| Nicosulfuron | | 40.1 |

The results show that each of the benzoic acid esters was as effective as the commercial adjuvant Atplus®411F but at very reduced rates of adjuvant for nicosulfruon.

Example 20 Use of Benzoic Acid Ester Adjuvants in Agrochemical Compositions Comprising Fomesafen The aromatic esters Finsolv® TN and the aromatic ester ethoxylate Dermol 25-3B were tested in a glasshouse against four weed species using the herbicide fomesafen.

An agrochemical composition was prepared containing either 0.2, 0.1, 0.05 or 0.025% v/v of the adjuvant in a track sprayer and was applied at a volume of 200 liters per hectare. The commercial adjuvant Turbocharge® was applied at 0.5% v/v. An agrochemical composition was prepared containing 0.2% v/v of the adjuvant in a track sprayer and was applied at a volume of 200 liters per hectare. Fomesafen was applied at either 60 or 120 grams of pesticide per hectare on each of the weed species. The weed species and their growth stage at spraying were *Polygonum convolvulus* (POLCO; growth stage 13-14), *Brachiaria plantaginea* (BRAL; growth stage 12-13), *Digitaria sanguinalis* (DIGSA; growth stage 13), and *Commelina benghalensis* (COMBE; growth stage 12).

Each spray test was replicated three times. The efficacy of the herbicide was assessed visually and expressed as a percentage of the leaf area killed. Samples were assessed at time periods of 14 and 21 days following application. The results shown in Table 24 below are mean averages over the two rates of fomesafen, three replicates the two assessment timings, and the four weed species, and are compared to the efficacy of fomesafen in the absence of an adjuvant, and fomesafen in the presence of the commercially available adjuvant Turbocharge®.

TABLE 24

Mean percentage kill results for fomesafen in the presence and
absence of Finsolv ®TN and the aromatic ester ethoxylate
Dermol 25-3B or Turbocharge ®. A standard Tukey HSD test
was carried out to assess whether each result was statistically
different from the other results and this is expressed as a letter:
tests with the same letter are not statistically different (p < 0.05).

| Treatment | Adjuvant rate % v/v | Mean across species |
|---|---|---|
| Fomesafen + Dermol ® 25-3B | 0.2 | 39.2A |
| Fomesafen + Dermol ® 25-3B | 0.1 | 33.4AB |
| Fomesafen + Turbocharge ® | 0.5 | 33.1ABC |
| Fomesafen + FINSOLV ®TN | 0.2 | 29.9BCD |
| Fomesafen + Dermol ® 25-3B | 0.05 | 24.4CDE |
| Fomesafen + FINSOLV ®TN | 0.1 | 24.3DE |
| Fomesafen + FINSOLV ®TN | 0.05 | 22.9DE |
| Fomesafen + Dermol ® 25-3B | 0.025 | 22.6DE |
| Fomesafen + FINSOLV ®TN | 0.025 | 21.5DE |

TABLE 24-continued

Mean percentage kill results for fomesafen in the presence and
absence of Finsolv ®TN and the aromatic ester ethoxylate
Dermol 25-3B or Turbocharge ®. A standard Tukey HSD test
was carried out to assess whether each result was statistically
different from the other results and this is expressed as a letter:
tests with the same letter are not statistically different (p < 0.05).

| Treatment | Adjuvant rate % v/v | Mean across species |
|---|---|---|
| Fomesafen | | 17.8E |

The results demonstrate that all of the benzoic acid esters tested are effective as adjuvants for fomesafen and that Finsolv SB and Dermol 25-3B are as effective as the commercially available agrochemical adjuvant Turbocharge® but at a much lower use rate of the adjuvant.

Example 21 Use of Benzoic Acid Ester Adjuvants in Agrochemical Compositions Comprising Mesotrione The aromatic esters Finsolv® SB (stearyl benzoate), Finsolv® TN and the aromatic ester ethoxylate Dermol 25-3B were tested in a glasshouse against three weed species using the herbicide mesotrione.

An agrochemical composition was prepared containing either 0.2, 0.1, 0.05 or 0.025% v/v of the adjuvant in a track sprayer and was applied at a volume of 200 liters per hectare. The commercial adjuvant Tween20® was applied at 0.2% v/v. Mesotrione was applied at either 60 or 120 grams of pesticide per hectare on weeds which had been grown to the 1.3 or 1.4 leaf stage. The commercially available surfactant Tetronic® 1107 was used in the spray tank at a concentration of 0.036 g/l alongside the lower concentration of mesotrione and at a concentration of 0.072 g/l at the higher concentration of mesotrione. The weed species were *Polygonum convolvulus* (POLCO) 13, *Brachiaria platyphylla* (BRAPL) 12-13, *Comelina berghalensis* (COMBE) 12 and *Digitaria sanguinalis* (DIGSA) 13.

Each spray test was replicated three times. The efficacy of the herbicide was assessed visually and expressed as a percentage of the leaf area killed. Samples were assessed at time periods of 14 and 21 days following application. The results shown in Table 25 below are mean averages over the two rates of mesotrione, three replicates, four weed species and the two assessment timings. The adjuvants are compared to the efficacy of mesotrione in the absence of adjuvant and mesotrione in the presence of the well-known adjuvant Tween®20.

TABLE 25

Mean percentage kill results for mesotrione in the presence and
absence of Finsolv ®TN and the aromatic ester ethoxylate
Dermol ®25-3B or Tween ®20. A standard Tukey HSD
test was carried out to assess whether each result was statistically
different from the other results and this is expressed as a letter:
tests with the same letter are not statistically different (p < 0.05).

| Treatment | Adjuvant rate % v/v | Mean across species |
|---|---|---|
| Mesotrione + FINSOLV ®TN | 0.2 | 70.1A |
| Mesotrione + Dermol ® 25-3B | 0.2 | 69.7A |
| Mesotrione + Dermol ® 25-3B | 0.1 | 69.6AB |
| Mesotrione + Tween20 ® | 0.2 | 66.8AB |
| Mesotrione + FINSOLV ®TN | 0.1 | 65AB |
| Mesotrione + Dermol ® 25-3B | 0.05 | 61.5BC |

TABLE 25-continued

Mean percentage kill results for mesotrione in the presence and absence of Finsolv ®TN and the aromatic ester ethoxylate Dermol ®25-3B or Tween ®20. A standard Tukey HSD test was carried out to assess whether each result was statistically different from the other results and this is expressed as a letter: tests with the same letter are not statistically different (p < 0.05).

| Treatment | Adjuvant rate % v/v | Mean across species |
| --- | --- | --- |
| Mesotrione + Dermol ® 25-3B | 0.025 | 56.9C |
| Mesotrione + FINSOLV ®TN | 0.025 | 55.3C |
| Mesotrione + FINSOLV ®TN | 0.05 | 55.2C |
| Mesotrione | | 33.7D |

The results show that all of the benzoic acid esters are effective adjuvants for mesotrione, and that they are as effective as the commercial Adjuvant Tween®20 at a much lower rate of adjuvant.

Example 22 Synthesis of Novel Adjuvants Benzoate 2 and Benzoate 3

In this example the novel compounds oleyl-2-ethoxy-benzoate and oleyl-10-ethoxy-benzoate are synthesised. The adjuvant mixture "Benzoate 2" was synthesised by adding an ethoxylated surfactant (Brij® O-2) comprising a mixture of linear long chain (primarily oleyl, 18 carbons in length) alcohols to a flask and reacting this oil with benzoyl chloride. The resulting mixture was extracted after the reaction and purified. Analysis by nmr showed that the product consisted of long-chain (18 carbons in length) alcohol ethoxylates with a terminal benzoate. Similarly the surfactant Brij® O-10 was reacted with benzoyl chloride to form the benzoate "Benzoate 3". These benzoic acid esters were tested as adjuvants in Examples 23, 24, 25, and 26 described infra.

Example 23 Use of Benzoic Acid Ester Adjuvants in Agrochemical Compositions Comprising Pinoxaden The two aromatic esters prepared in example 22 tested in a glasshouse against four weed species using the herbicide pinoxaden.

An agrochemical composition was prepared containing 0.2% v/v of the adjuvant in a track sprayer and was applied at a volume of 200 liters per hectare. Pinoxaden was applied at either 7.5 or 15 grams of pesticide per hectare on each of the weed species. The commercially available surfactant Atlas® G5000 was used in the spray tank at a concentration of 0.00375 g/l alongside the lower concentration of pinoxaden and at a concentration of 0.0075 g/l at the higher concentration of pinoxaden. The weed species and their growth stage at spraying were *Alopecurus myosuroides* (ALOMY; growth stage 13), *Avena fatua* (AVEFA; growth stage 12); *Lolium perenne* (LOLPE; growth stage 13), *Setaria viridis* (SETVI; growth stage 13-14).

Each spray test was replicated three times. The efficacy of the herbicide was assessed visually and expressed as a percentage of the leaf area killed. Samples were assessed at time periods of 14 and 21 days following application. The results shown in Table 26 below are mean averages over the two rates of pinoxaden, three replicates and the two assessment timings, and are compared to the efficacy of pinoxaden in the absence of an adjuvant and pinoxaden in the presence of tris 2-ethylhexyl phosphate.

The results show that each of the benzoic acid esters tested is an effective adjuvant for pinoxaden, and that Benzoate 2 was particularly effective.

TABLE 26

Mean percentage kill results for pinoxaden in the presence and absence of Benzoate 2 and Benzoate 3 or TEHP. A standard Tukey HSD test was carried out to assess whether each result was statistically different from the other results and this is expressed as a letter: tests with the same letter are not statistically different (p < 0.05)..

| Treatment | Mean across species |
| --- | --- |
| Pinoxaden + TEHP | 80.6A |
| Pinoxaden + Benzoate 2 | 75.5A |
| Pinoxaden + Benzoate 3 | 66.5B |
| Pinoxaden | 4.0C |

Example 24 Use of Benzoic Acid Ester Adjuvants in Agrochemical Compositions Comprising Nicosulfuron The two aromatic esters prepared in example 22 tested in a glasshouse against four weed species using the herbicide nicosulfuron. Nicosulfuron was applied at either 30 or 60 grams of pesticide per hectare on each of the weed species. The weed species and their growth stage at spraying were *Abutilon theophrasti* (ABUTH; growth stage 13), *Chenopodium album* (CHEAL; growth stage 14-15), *Digitaria sanguinalis* (DIGSA; growth stage 14), and *Setaria viridis* (SETVI; growth stage 13-14).

Each spray test replicated three times. The efficacy of the herbicide was assessed visually and expressed as a percentage of the leaf area killed. Samples were assessed at time periods of 14 and 21 days following application. The results shown in Table 27 below are mean averages over the two rates of nicosulfuron, three replicates and the two assessment timings, and are compared to the efficacy of nicosulfuron in the absence of an adjuvant, and nicosulfuron in the presence of the commercially available tank-mix adjuvant, Atplus411F®.

TABLE 27

Mean percentage kill results for nicosulfuron in the presence and absence of Benzoate 2 and Benzoate 3. A standard Tukey HSD test was carried out to assess whether each result was statistically different from the other results and this is expressed as a letter: tests with the same letter are not statistically different (p < 0.05).

| Treatment | Mean across species |
| --- | --- |
| Nicosulfuron + Atplus 411F | 69.2A |
| Pinoxaden + Benzoate 2 | 65.6AB |
| Pinoxaden + Benzoate 3 | 61.2B |
| Pinoxaden | 46.6C |

The results show that each of the benzoic acid ester is effective as an adjuvant for nicosulfruon.

Example 25 Use of Benzoic Acid Ester Adjuvants in Agrochemical Compositions Comprising Fomesafen The two aromatic esters prepared in example 22 tested in a glasshouse against four weed species using the herbicide fomesafen.

An agrochemical composition was prepared containing 0.2% v/v of the adjuvant in a track sprayer and was applied at a volume of 200 liters per hectare. Fomesafen was applied at either 60 or 120 grams of pesticide per hectare on each of the weed species. The weed species and their growth stage at spraying were *Polygonum convolvulus* (POLCO; growth stage 13), *Brachiaria plantaginea* (BRAL; growth stage 13), *Digitaria sanguinalis* (DIGSA; growth stage 12-13), and *Commelina benghalensis* (COMBE; growth stage 11-12).

Each spray test was replicated three times. The efficacy of the herbicide was assessed visually and expressed as a percentage of the leaf area killed. Samples were assessed at time periods of 14 and 21 days following application. The results shown in Table 28 below are mean averages over the two rates of fomesafen, three replicates the two assessment timings, and the four weed species, and are compared to the efficacy of fomesafen in the absence of an adjuvant, and fomesafen in the presence of the commercially available adjuvant Turbocharge®.

TABLE 28

Mean percentage kill results for fomesafen in the presence and absence of Benzoate 2 and Benzoate 3 or Turbocharge ®. A standard Tukey HSD test was carried out to assess whether each result was statistically different from the other results and this is expressed as a letter: tests with the same letter are not statistically different (p < 0.05).

| Treatment | Mean across species |
| --- | --- |
| Fomesafen + Benzoate 2 | 57.5A |
| Fomesafen + Turbocharge | 51.5B |
| Fomesafen + Benzoate 3 | 48.9B |
| Fomesafen | 32.8C |

The results demonstrate that all of the benzoic acid esters tested are effective as adjuvants for fomesafen and that Finsolv SB and Dermol 25-3B are as effective as the commercially available agrochemical adjuvant Turbocharge®.

Example 26 Use of Benzoic Acid Ester Adjuvants in Agrochemical Compositions Comprising Mesotrione The two aromatic esters prepared in example 22 tested in a glasshouse against four weed species using the herbicide mesotrione.

An agrochemical composition was prepared containing 0.2% v/v of the adjuvant in a track sprayer and was applied at a volume of 200 liters per hectare. Mesotrione was applied at either 60 or 120 grams of pesticide per hectare on weeds which had been grown to the 1.3 or 1.4 leaf stage. The commercially available surfactant Tetronic® 1107 was used in the spray tank at a concentration of 0.036 g/l alongside the lower concentration of mesotrione and at a concentration of 0.072 g/l at the higher concentration of mesotrione. The weed species were *Xanthium strumarium* (XANST), *Brachiaria platyphylla* (BRAPL), and *Digitaria sanguinalis* (DIGSA).

Each spray test was replicated three times. The efficacy of the herbicide was assessed visually and expressed as a percentage of the leaf area killed. Samples were assessed at time periods of 14 and 21 days following application. The results shown in Table 29 below are mean averages over the two rates of mesotrione, three replicates and the two assessment timings, and are compared to the efficacy of mesotrione in the absence of adjuvant and mesotrione in the presence of the well-known adjuvant Tween®20. The results shown in Table 29 below are mean averages over the two rates of mesotrione, three replicates, three assessment timings and three weed species. The results are compared to the efficacy of mesotrione in the absence of an adjuvant and mesotrione in the presence of the commercially available adjuvant Tween®20.

TABLE 29

Mean percentage kill results for mesotrione in the presence and absence of Benzoate 2 and Benzoate 3 or Tween ®20. A standard Tukey HSD test was carried out to assess whether each result was statistically different from the other results and this is expressed as a letter: tests with the same letter are not statistically different (p < 0.05).

| Treatment | Mean across species |
| --- | --- |
| Mesotrione + Benzoate 2 | 61.4A |
| Mesotrione + Tween20 | 60.8AB |
| Mesotrione + Benzoate 3 | 55.5B |
| Mesotrione | 39.4C |

The results show that the two benzoic acid esters are effective adjuvants for mesotrione, and that Benzoate 2 was particularly effective.

Example 27 A Further Example of a Novel Benzoate Capped Ethoxylated Adjuvant

The commercial product Arosurf® 66E20 (branched C18 alcohol ethoxylate with an average of 20 moles of ethoxylate) was reacted with benzoyl chloride. The product of this reaction was purified by chromatography and shown by nmr analysis to have a terminal benzoate ester group on the ethoxylate.

Example 28 Use of Benzoic Acid Ester Adjuvants in Agrochemical Compositions Comprising Isopyrazam The efficacy of the benzoic acid esters Finsolv® SB, and the benzoate end capped ethoxylate Dermol®25-3B as adjuvants in compositions comprising isopyrazam was tested and compared to the standard formulations (both EC and SC) of the fungicide, which lack this type of adjuvant.

Wheat plants were inoculated with the fungus *Septoria tritici*. Four days after inoculation the plants were sprayed with a diluted emulsion concentrate or suspension concentrate formulation of the fungicide isopyrazam at rates of 3, 10, 30 and 100 mg of the fungicide per liter of spray solution, using a laboratory track sprayer which delivered the spray at a rate of 200 liters per hectare. Spray tests were also carried out with diluted suspension concentrate additionally comprising each of the benzoate adjuvants described above. These adjuvants were added to the spray solution at a rate of 0.2% w/w, based on the quantity of spray liquor. The leaves of the plants were assessed visually 14 days after the spray application and the damage was expressed as the percentage of the leaf area infected. Each spray test was replicated three times across the four application rates and the modelled means of these results are shown in Table 30 below.

As can be seen from Table 30 the inclusion of a benzoate as an adjuvant for isopyrazam resulted in a significant reduction in the percentage of infection by *S. tritici* in comparison to that achieved by the standard isopyrazam SC. As well as increasing the efficacy of the standard suspension concentrate formulation (Standard SC) of isopyrazam, inclusion of the benzoate adjuvants Finsolv® SB or Dermol 25-3B also resulted in isopyrazam compositions that were as effective at controlling S. triticias the standard isopyrazam emulsion concentrate formulation (Standard EC).

TABLE 30

Mean % infection of wheat plants with S. tritici treated with isopyrazam in the presence and absence of benzoic acid ester adjuvants. A standard Tukey HSD test was carried out to assess whether each result was statistically different from the other results and this is expressed as a letter: tests with the same letter are not statistically different (p < 0.05).

| Treatment | Mean % infection |
| --- | --- |
| Control (blank) | 60 A |
| Standard Isopyrazam SC | 38.6 B |
| Standard Isopyrazam SC plus Dermol 25-3B | 26.2 C |
| Standard Isopyrazam EC | 25.7 C |
| Standard Isopyrazam SC plus Finsolv SB | 25.4 C |

Example 29 Use of Benzoic Acid Ester Adjuvants in Agrochemical Compositions Comprising Epoxyconazole The efficacy of the benzoic acid ester Finsolv® SB, and the benzoate end capped ethoxylate Dermol®25-3B as adjuvants in compositions comprising isopyrazam was tested and as adjuvants in compositions comprising epoxyconazole, was tested and compared to the standard formulation (SC) of the fungicide, which lacks this type of adjuvant.

Wheat plants were inoculated with the fungus Septoria tritici. Four days after inoculation the plants were sprayed with a diluted suspension concentrate formulation of the fungicide epoxyconazole at rates of 3, 10, 30 and 100 mg of the fungicide per liter of spray solution, using a laboratory track sprayer which delivered the spray at a rate of 200 liters per hectare. Spray tests were also carried out with diluted suspension concentrate additionally comprising each of the benzoate adjuvants described above. These adjuvants were added to the spray solution at a rate of 0.2% w/w, based on the quantity of spray liquor. The leaves of the plants were assessed visually 14 days after the spray application and the damage was expressed as the percentage of the leaf area infected. Each spray test was replicated three times across the four application rates and the modelled means of these results are shown in Table 31 below.

TABLE 31

Mean % infection of wheat plants with S. tritici treated with epoxyconazole in the presence and absence of benzoic acid ester adjuvants. A standard Tukey HSD test was carried out to assess whether each result was statistically different from the other results and this is expressed as a letter: tests with the same letter are not statistically different (p < 0.05).

| Treatment | Mean % infection |
| --- | --- |
| Control (blank) | 57.6 A |
| Standard epoxyconazole SC | 44.5 A |
| Standard epoxyconazole SC + Finsolv SB | 18.7 B |
| Standard epoxyconazole SC + Dermol 25-3B | 10.8 C |

The results show that the mean percentage infection with S. tritici is reduced further when the wheat plants were treated with compositions of epoxyconazole comprising each of the benzoates, in comparison to the control (blank) and when treated with the standard SC composition of epoxyconazole. This shows that the benzoates are effective adjuvants for epoxyconazole.

Example 30

Sunspray 11N is a commercially available oil which can be used to formulate adjuvants for tank mixing with agrochemical peroducts. One of the problems with ethoxylated adjuvants is that they are often incompatible with such oils and cannot therefore be formulated with this oil. This is a limitation. An advantage of a benzoate ester end capped adjuvant is that it has excellent compatibility with oils such as Sunspray 11N. Equal portions were prepared of Sunspray 11N and either Oleyl 10 ethoxylate with a butyl end cap (Agnique OC9 FOH 10B) or oleyl 12 ethoxylate with a benzoate end cap. The Agnique FOH OC9 10B formed two distinct layers whereas the benzoate end cap formed a single layer.

This demonstrates the superior miscibility of benzoate end capped adjuvants to butyl end capped adjuvants.

Example 31 Further Benzoate End Capped Ethoxylated Surfactants

The following commercially available ethoxylated surfactants were reacted with benzoyl chloride to form benzoate ester end capped adjuvants. The surfactants were dissolved in dichloromethane at which point triethylamine and benzoyl chloride were successively added. The mixture was stirred for 12 hours at 20 C. After this time the solvent was removed and the residue dissolved in ethyl acetate and aqueous sodium bicarbonate. The aqueous layer was washed with ethyl acetate which was then dried over anhydrous magnesium sulphate, filtered and concentrated. The product was identified by nmr spectroscopy.

| Surfactant | Formula of product | Reaction yield % |
|---|---|---|
| Brij 98V | $C_{18}H_{35}(OCH_2CH_2)_{20}$—OCOPh | 99 |
| Genapol O 120 | $C_{18}H_{35}(OCH_2CH_2)_{12}$—OCOPh | 94 |
| Brij 92V | $C_{18}H_{35}(OCH_2CH_2)_2$—OCOPh | 100 |
| Arosurf 66E12 | $C_{18}H_{37}(OCH_2CH_2)_{12}$—OCOPh | 91 |
| Arosurf 66E10 | $C_{18}H_{37}(OCH_2CH_2)_{10}$—OCOPh | 87 |
| Synperonic 13/5 | $C_{13}H_{27}(OCH_2CH_2)_5$—OCOPh | 72 |

Example 32 Use of Benzoic Acid Ester Adjuvants in Agrochemical Compositions Comprising Pinoxaden The aromatic compound tridecyl salicylate was tested in a glasshouse against four weed species using the herbicide pinoxaden.

An agrochemical composition was prepared containing 0.2% v/v of the adjuvant in a track sprayer and was applied at a volume of 200 liters per hectare. Pinoxaden was applied at either 7.5 or 15 grams of pesticide per hectare on each of the weed species. The commercially available surfactant Atlas® G5000 was used in the spray tank at a concentration of 0.00375 g/l alongside the lower concentration of pinoxaden and at a concentration of 0.0075 g/l at the higher concentration of pinoxaden. The weed species and their growth stage at spraying were *Alopecurus myosuroides* (ALOMY; growth stage 13), *Avena fatua* (AVEFA; growth stage 12); *Lolium perenne* (LOLPE; growth stage 13), *Setaria viridis* (SETVI; growth stage 13-14).

Each spray test was replicated three times. The efficacy of the herbicide was assessed visually and expressed as a percentage of the leaf area killed. Samples were assessed at time periods of 14 and 21 days following application. The results shown in Table 18 below are mean averages over the two rates of pinoxaden, three replicates and the two assessment timings, and are compared to the efficacy of pinoxaden in the absence of an adjuvant and pinoxaden in the presence of tris 2-ethylhexyl phosphate (TEHP).

The results show that tridecyl salicylate is an effective adjuvant for pinoxaden.

TABLE 32

Mean percentage kill results for pinoxaden in the presence and absence of tridecyl salicylate or TEHP. A standard Tukey HSD test was carried out to assess whether each result was statistically different from the other results and this is expressed as a letter: tests with the same letter are not statistically different ($p < 0.05$)..

| Treatment | Mean across species |
| --- | --- |
| Pinoxaden + TEHP | 86.1A |
| Pinoxaden + Tridecyl salicylate | 85A |
| Pinoxaden | 3.6B |

Example 33 Use of Benzoic Acid Ester Adjuvants in Agrochemical Compositions Comprising Nicosulfuron The aromatic compound tridecyl salicylate was tested in a glasshouse against four weed species using the herbicide nicosulfuron. Nicosulfuron was applied at either 30 or 60 grams of pesticide per hectare on each of the weed species. The weed species and their growth stage at spraying were *Abutilon theophrasti* (ABUTH; growth stage 13), *Chenopodium album* (CHEAL; growth stage 14-15), *Digitaria sanguinalis* (DIGSA; growth stage 14), and *Setaria viridis* (SETVI; growth stage 13-14).

Each spray test replicated three times. The efficacy of the herbicide was assessed visually and expressed as a percentage of the leaf area killed. Samples were assessed at time periods of 14 and 21 days following application. The results shown in Table 19 below are mean averages over the two rates of nicosulfuron, three replicates and the two assessment timings, and are compared to the efficacy of nicosulfuron in the absence of an adjuvant, and nicosulfuron in the presence of the commercially available tank-mix adjuvant, Atplus411F®.

TABLE 33

Mean percentage kill results for nicosulfuron in the presence and absence of tridecyl salicylate. A standard Tukey HSD test was carried out to assess whether each result was statistically different from the other results and this is expressed as a letter: tests with the same letter are not statistically different ($p < 0.05$).

| Treatment | Mean across species |
| --- | --- |
| Nicosulfuron + ATPLUS 411 F ® | 63.1A |
| Nicosulfuron + Tridecyl salicylate | 61.5A |
| Nicosulfuron | 40.1B |

The results show that tridecyl salicylate is effective as an adjuvant for nicosulfruon.

Example 34 Use of Benzoic Acid Ester Adjuvants in Agrochemical Compositions Comprising Fomesafen The aromatic compound tridecyl salicylate was tested in a glasshouse against four weed species using the herbicide fomesafen.

An agrochemical composition was prepared containing 0.2% v/v of the adjuvant in a track sprayer and was applied at a volume of 200 liters per hectare. Fomesafen was applied at either 60 or 120 grams of pesticide per hectare on each of the weed species. The weed species and their growth stage at spraying were *Polygonum convolvulus* (POLCO; growth stage 13-14), *Brachiaria plantaginea* (BRAL; growth stage 13-14), *Digitaria sanguinalis* (DIGSA; growth stage 14), and *Commelina benghalensis* (COMBE; growth stage 13-14).

Each spray test was replicated three times. The efficacy of the herbicide was assessed visually and expressed as a percentage of the leaf area killed. Samples were assessed at time periods of 14 and 21 days following application. The results shown in Table 34 below are mean averages over the two rates of fomesafen, three replicates the two assessment timings, and the four weed species, and are compared to the efficacy of fomesafen in the absence of an adjuvant, and fomesafen in the presence of the commercially available adjuvant Turbocharge®.

TABLE 34

Mean percentage kill results for fomesafen in the presence and absence of tridecyl salicylate or Turbocharge ®. A standard Tukey HSD test was carried out to assess whether each result was statistically different from the other results and this is expressed as a letter: tests with the same letter are not statistically different ($p < 0.05$).

| Treatment | Mean across species |
| --- | --- |
| Fomesafen + Turbocharge ® | 33.0A |
| Fomesafen + Tridecyl salicylate | 28.2A |
| Fomesafen | 17.8B |

The results demonstrate that tridecyl salicylate is effective as adjuvants for fomesafen

Example 35 Use of Benzoic Acid Ester Adjuvants in Agrochemical Compositions Comprising Mesotrione The aromatic compound tridecyl salicylate was tested in a glasshouse against three weed species using the herbicide mesotrione.

An agrochemical composition was prepared containing 0.2% v/v of the adjuvant in a track sprayer and was applied at a volume of 200 liters per hectare. Mesotrione was applied at either 60 or 120 grams of pesticide per hectare on weeds which had been grown to the 1.3 or 1.4 leaf stage. The commercially available surfactant Tetronic® 1107 was used in the spray tank at a concentration of 0.036 g/l alongside the lower concentration of mesotrione and at a concentration of 0.072 g/l at the higher concentration of mesotrione. The weed species were *Xanthium strumarium* (XANST), *Brachiaria platyphylla* (BRAPL), and *Digitaria sanguinalis* (DIGSA).

Each spray test was replicated three times. The efficacy of the herbicide was assessed visually and expressed as a percentage of the leaf area killed. Samples were assessed at time periods of 14 and 21 days following application. The results shown in Table 10 below are mean averages over the two rates of mesotrione, three replicates and the two assessment timings, and are compared to the efficacy of mesotrione in the absence of adjuvant and mesotrione in the presence of the well-known adjuvant Tween®20. The results shown in Table 16 below are mean averages over the two rates of mesotrione, three replicates, three assessment timings and three weed species. The results are compared to the efficacy of mesotrione in the absence of an adjuvant and mesotrione in the presence of the commercially available adjuvant Tween®20.

TABLE 35

Mean percentage kill results for mesotrione in the presence and absence of tridecyl salicylate or Tween ®20. A standard Tukey HSD test was carried out to assess whether each result was statistically different from the other results and this is expressed as a letter: tests with the same letter are not statistically different (p < 0.05).

| Treatment | Mean across species |
|---|---|
| Mesotrione + Tween ®20 | 67.1A |
| Mesotrione + Tridecyl salicylate | 63.6A |
| Mesotrione | 33.8B |

The results show that tridecyl salicylate is an effective adjuvant for mesotrione.

Example 36 Use of Aromatic Ester Adjuvants in Agrochemical Compositions Containing Abamectin The efficacy of the benzoic acid esters Finsolv® SB (isostearyl benzoate) and Finsolv® TN ($C_{12}$-$C_{15}$ alkyl benzoate) and the aromatic ester ethoxylate Dermol®25-3B ($C_{12}$-$C_{15}$ alkyl ethoxy (3) benzoate) as adjuvants in compositions containing abamectin was tested and compared to the efficacy of abamectin compositions which lack this type of adjuvant. The adjuvants were present at 0.1% v/v in the abamectin compositions. The surfactants polyoxyethylene sorbitan monooleate and an ethoxylated castor oil were also present in all the abamectin compositions tested.

Two week old French bean (*Phaseolus vulgaris*) plants were infested with a mixed population of two spotted spider mite *Tetranychus urticae*. One day after infestation the plants were treated with the test compositions, with a track sprayer from the top with a rate of 200 liters per hectare. Plants were incubated in the greenhouse for 10 days and the evaluation was done on mortality against Larva and Adults, just on the lower side (untreated) of the leaves. Each experiment was replicated twice and the results were averaged. The mortality against Larva and Adults was then averaged.

In the control experiment the beans were sprayed with water and no mortality was observed. The beans were sprayed with aromatic ester compositions without abamectin present, containing 0.1% v/v Finsolv® TN, 0.1% v/v Finsolv® SB or 0.1% v/v Dermol® 25-3B and no mortality was observed in each case.

As can be seen from Table 36 the inclusion of the aromatic esters as adjuvants for abamectin provided effective control of *Tetranychus urticae* at much lower concentrations of abamectin than are required in the absence of adjuvant.

The invention claimed is:

1. An agrochemical formulation concentrate composition suitable for further dilution wherein the composition is an emulsion concentrate (EC), a suspension of particles in water (SC), a dispersion concentrate (DC), a suspension of particles in an emulsion (SE), or a suspension of particles in oil (OD) comprising:
   i. an agrochemical active ingredient selected from a herbicide, a molluscicide, a fungicide, a plant growth regulator, and a safener, or a combination thereof;
   ii. a surfactant;
   iii. an adjuvant, wherein the adjuvant is an aromatic ester of formula (I)

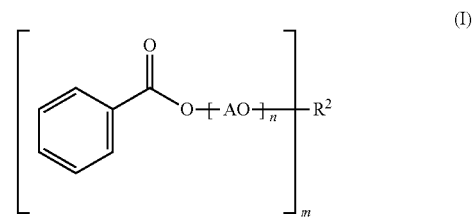

wherein
   n is an integer selected from 0 to 20 inclusive,
   each A is independently $C_{1-10}$alkanediyl,
   m is an integer selected from 1, 2 or 3;
   wherein when m is 1, $R^2$ is selected from the group consisting of $C_7$-$C_{20}$alkyl, $C_7$-$C_{20}$ alkenyl, $C_7$-$C_{20}$ alkyldienyl and $C_7$-$C_{20}$ alkyltrienyl; and when m is 2 or 3, $R^2$ is selected from the group consisting of $C_1$-$C_{20}$ alkyl, $C_4$-$C_{22}$ alkenyl, $C_4$-$C_{22}$ alkyldienyl and $C_6$-$C_{22}$ alkyltrienyl; and
   each m group is independently attached to any carbon atom within $R^2$, and each A and n is independently as defined above provided that the compound of formula (I) is not dipropylene glycol dibenzoate; and
   iv. a solvent.

2. The agrochemical formulation concentrate composition according to claim 1, wherein n is 1.

3. The agrochemical formulation concentrate composition according to claim 1, wherein each A is independently ethanediyl, propanediyl, butanediyl or butanediyl.

TABLE 36

% Mortality of *Tetranychus urticae* treated with abamectin in the presence and absence of aromatic ester adjuvants.

| Treatment | % mortality of *Tetranychus urticae* at different abamectin concentrations (ppm) | | | | | | | | |
|---|---|---|---|---|---|---|---|---|---|
| | 3 ppm | 1.5 ppm | 0.8 ppm | 0.4 ppm | 0.2 ppm | 0.1 ppm | 0.05 ppm | 0.025 ppm | 0.0125 ppm |
| Abamectin | 95 | 70 | 27 | 0 | 0 | | | | |
| Abamectin + FINSOLV ® TN | | | | | 100 | 90 | 60 | 50 | 47 |
| Abamectin + FINSOLV ® SB | | | | | 100 | 99 | 75 | 65 | 50 |
| Abamectin + Dermol ® 25-3B | | | | | 100 | 99 | 75 | 60 | 0 |

4. The agrochemical formulation concentrate composition according to claim 1, wherein each A is independently each A is independently 1,2-ethanediyl, 1,2-propanediyl, 1,2-butanediyl or 1,4-butanediyl.

5. The agrochemical formulation concentrate composition according to claim 1, wherein n is 0.

6. The agrochemical formulation concentrate composition according to claim 1, wherein m is 1.

7. The agrochemical formulation concentrate composition according to claim 6, wherein $R^2$ is $C_8$-$C_{18}$ alkyl.

8. The agrochemical formulation concentrate composition according to claim 7, wherein $R^2$ is 2-ethylhexyl, $C_{12}$ alkyl, $C_{13}$ alkyl, $C_{14}$ alkyl, $C_{15}$ alkyl, $C_{16}$ alkyl, $C_{17}$ alkyl, oleyl or isooctadecyl.

9. The agrochemical formulation concentrate composition according to claim 1, wherein m is 2.

10. The agrochemical formulation concentrate composition according to claim 9, wherein $R^2$ is $C_7$-$C_{18}$ alkyl.

11. The agrochemical formulation concentrate composition according to claim 10, wherein $R^2$ is a $C_8$ branched-chain alkyl, and each m group is attached to a different carbon atom in $R^2$.

12. The agrochemical formulation concentrate composition according to claim 1, wherein the compound of formula (I) is 2,2,4-trimethyl-1,3-pentanediol dibenzoate.

13. The agrochemical formulation concentrate composition according to claim 1, wherein the active ingredient is present at a concentration in the range from about 0.001% to about 90% w/w.

14. The agrochemical formulation concentrate composition according to claim 1, wherein the active ingredient is selected from the group consisting of: bicyclopyrone, mesotrione, fomesafen, tralkoxydim, napropamide, amitraz, propanil, pyrimethanil, dicloran, tecnazene, toclofos methyl, flamprop M, 2,4-D, MCPA, mecoprop, clodinafop-propargyl, cyhalofop-butyl, diclofop methyl, haloxyfop, quizalofop-P, indol-3-ylacetic acid, 1-naphthylacetic acid, isoxaben, tebutam, chlorthal dimethyl, benomyl, benfuresate, dicamba, dichlobenil, benazolin, triazoxide, fluazuron, teflubenzuron, phenmedipham, acetochlor, alachlor, metolachlor, pretilachlor, thenylchlor, alloxydim, butroxydim, clethodim, cyclodim, sethoxydim, tepraloxydim, pendimethalin, dinoterb, bifenox, oxyfluorfen, acifluorfen, fluoroglycofen-ethyl, bromoxynil, ioxynil, imazamethabenz-methyl, imazapyr, imazaquin, imazethapyr, imazapic, imazamox, flumioxazin, flumiclorac-pentyl, picloram, amodosulfuron, chlorsulfuron, nicosulfuron, rimsulfuron, triasulfuron, triallate, pebulate, prosulfocarb, molinate, atrazine, simazine, cyanazine, ametryn, prometryn, terbuthylazine, terbutryn, sulcotrione, isoproturon, linuron, fenuron, chlorotoluron, metoxuron, isopyrazam, mandipropamid, azoxystrobin, trifloxystrobin, kresoxim methyl, famoxadone, metominostrobin and picoxystrobin, cyprodanil, carbendazim, thiabendazole, dimethomorph, vinclozolin, iprodione, dithiocarbamate, imazalil, prochloraz, fluquinconazole, epoxiconazole, flutriafol, azaconazole, bitertanol, bromuconazole, cyproconazole, difenoconazole, hexaconazole, paclobutrazole, propiconazole, tebuconazole, triadimefon, trtiticonazole, fenpropimorph, tridemorph, fenpropidin, mancozeb, metiram, chlorothalonil, thiram, ziram, captafol, captan, folpet, fluazinam, flutolanil, carboxin, metalaxyl, bupirimate, ethirimol, dimoxystrobin, fluoxastrobin, orysastrobin, metominostrobin, and prothioconazole.

15. The agrochemical formulation concentrate composition according to claim 1, comprising at least one additional component selected from the group consisting of agrochemicals, adjuvants, surfactants, and emulsifiers.

16. The agrochemical formulation concentrate according to claim 1 diluted or dispersed in water suitable for application in agriculture.

17. A method of controlling a pest, comprising applying a composition as defined in claim 1 to said pest or a locus of said pest.

18. A method of making an agrochemical a formulation concentrate composition suitable for further dilution wherein the composition is an emulsion concentrate (EC), a suspension of particles in water (SC), a dispersion concentrate (DC), a suspension of particles in an emulsion (SE), or a suspension of particles in oil (OD), the method comprising combining:
  i. an agrochemical active ingredient selected from a herbicide, a molluscicide, a fungicide, a plant growth regulator, and a safener, or a combination thereof;
  ii. a surfactant; and
  iii. an aromatic ester of formula (I) as defined in claim 1.

19. The method according to claim 18, wherein the agrochemical composition is as defined in claim 13.

20. The agrochemical formulation concentrate composition according to claim 1, wherein the aromatic ester of formula (I) comprises from 10% w/w to about 40% w/w of the total agrochemical formulation concentrate composition.

21. The method of claim 18, wherein the aromatic ester is present from 10% w/w to about 40% w/w of the total agrochemical formulation concentrate composition.

* * * * *